(12) United States Patent
Ishikawa

(10) Patent No.: US 10,445,897 B2
(45) Date of Patent: Oct. 15, 2019

(54) DEVICE FOR ACQUIRING INFORMATION RELATING TO POSITION DISPLACEMENT OF MULTIPLE IMAGE DATA SETS, METHOD, AND PROGRAM

(71) Applicant: CANON KABUSHIKI KAISHA, Tokyo (JP)

(72) Inventor: Ryo Ishikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/742,336

(22) PCT Filed: Jul. 4, 2016

(86) PCT No.: PCT/JP2016/003184
§ 371 (c)(1),
(2) Date: Jan. 5, 2018

(87) PCT Pub. No.: WO2017/006555
PCT Pub. Date: Jan. 12, 2017

(65) Prior Publication Data
US 2018/0204349 A1 Jul. 19, 2018

(30) Foreign Application Priority Data

Jul. 9, 2015 (JP) ................................. 2015-138112
Jul. 9, 2015 (JP) ................................. 2015-138113

(51) Int. Cl.
*G06K 9/00* (2006.01)
*G06T 7/73* (2017.01)
(Continued)

(52) U.S. Cl.
CPC .............. *G06T 7/74* (2017.01); *A61B 5/0095* (2013.01); *A61B 5/7207* (2013.01); *G01C 11/02* (2013.01); *G01C 11/06* (2013.01); *G06T 1/0007* (2013.01)

(58) Field of Classification Search
CPC ..... A61B 5/0095; A61B 5/7207; G01C 11/02; G01C 11/06; G06T 1/0007; G06T 7/74
See application file for complete search history.

(56) References Cited

U.S. PATENT DOCUMENTS

| 2010/0312113 A1 | 12/2010 | Ogasawara |
| 2013/0245418 A1* | 9/2013 | Oishi .................. A61B 5/0095 600/407 |

(Continued)

FOREIGN PATENT DOCUMENTS

| EP | 1782736 A1 | 5/2007 |
| JP | 2009-131420 A | 6/2009 |

(Continued)

OTHER PUBLICATIONS

Minghua Xu, et al., Universal back-projection algorithm for photoacoustic computed tomography, Physical Review E 71, 016706 (2005), Jan. 19, 2005, pp. 016706-1 to 016706-7, vol. 71, issue 016706, The American Physical Society, USA.

(Continued)

*Primary Examiner* — Xin Jia
(74) *Attorney, Agent, or Firm* — Canon U.S.A., Inc. IP Division

(57) ABSTRACT

An apparatus includes a first acquisition unit acquiring first multiple image data sets, a second acquisition unit acquiring first composited image data using first two or more image data sets of the first multiple image data sets, a third acquisition unit acquiring second composited volume data, using second two or more image data sets of the first multiple image data sets, the second two or more image data sets different from the first two or more image data sets, a fourth acquisition unit acquiring information relating to positional displacement between the first the second composited volume data, using the first the second composited image data, and a fifth acquisition unit acquiring information (Continued)

relating to positional displacement of the first multiple of image data sets, using information relating to the positional displacement between the first the second composited image data.

19 Claims, 12 Drawing Sheets

(51) Int. Cl.
*A61B 5/00* (2006.01)
*G01C 11/02* (2006.01)
*G01C 11/06* (2006.01)
*G06T 1/00* (2006.01)

(56) References Cited

U.S. PATENT DOCUMENTS

2013/0303909 A1* 11/2013 Kang .................. A61B 5/0095
600/443

2015/0073278 A1* 3/2015 Oyama ................ A61B 5/0037
600/449
2015/0351639 A1* 12/2015 Abe ..................... A61B 8/4416
600/407

FOREIGN PATENT DOCUMENTS

| JP | 2010-088496 A | 4/2010 |
| JP | 2011-125571 A | 6/2011 |
| JP | 2014140716 A | 8/2014 |

OTHER PUBLICATIONS

Y. Ueda, et al., Development of optical mammography based on analysis of time-resolved photon path distribution, Proc. of SPIE, 2010, pp. 756117-1 to 756117-6, vol. 7561, issue 17, International Society for Optics and Photonics, USA.

* cited by examiner

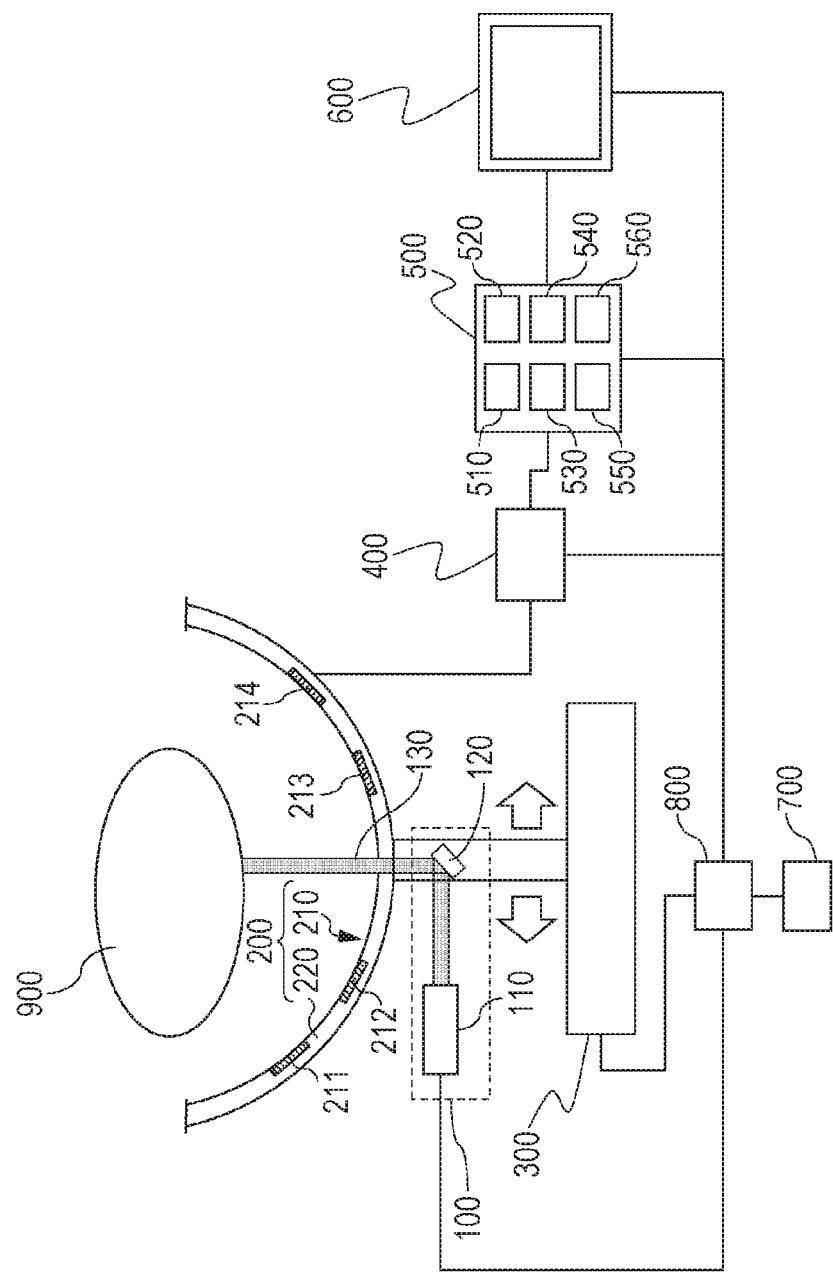
[Fig. 1]

[Fig. 2]
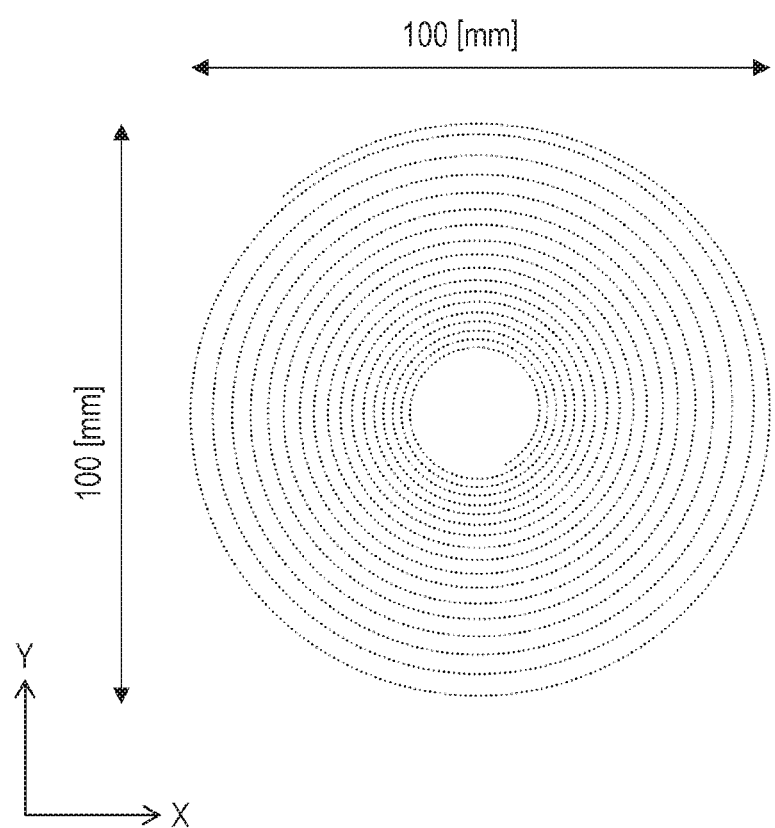

[Fig. 3]
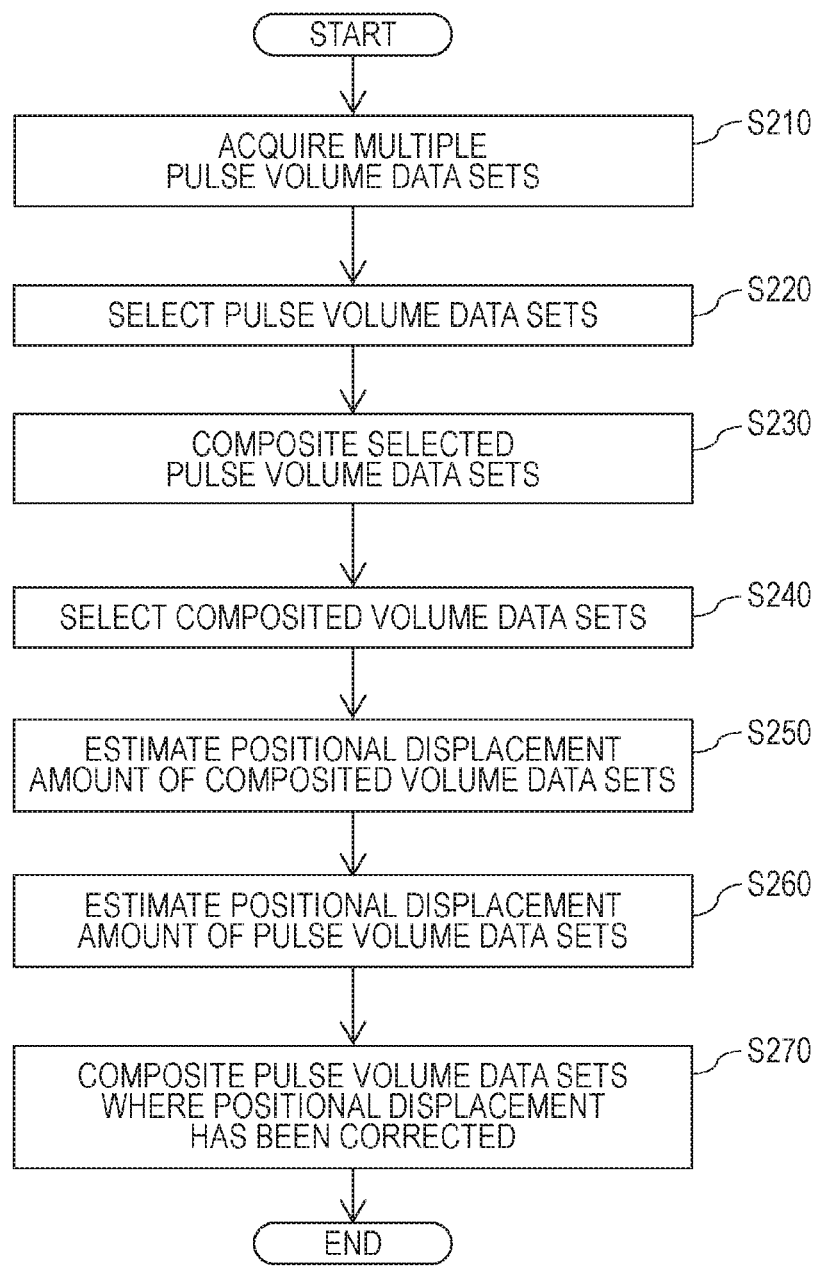

[Fig. 4]
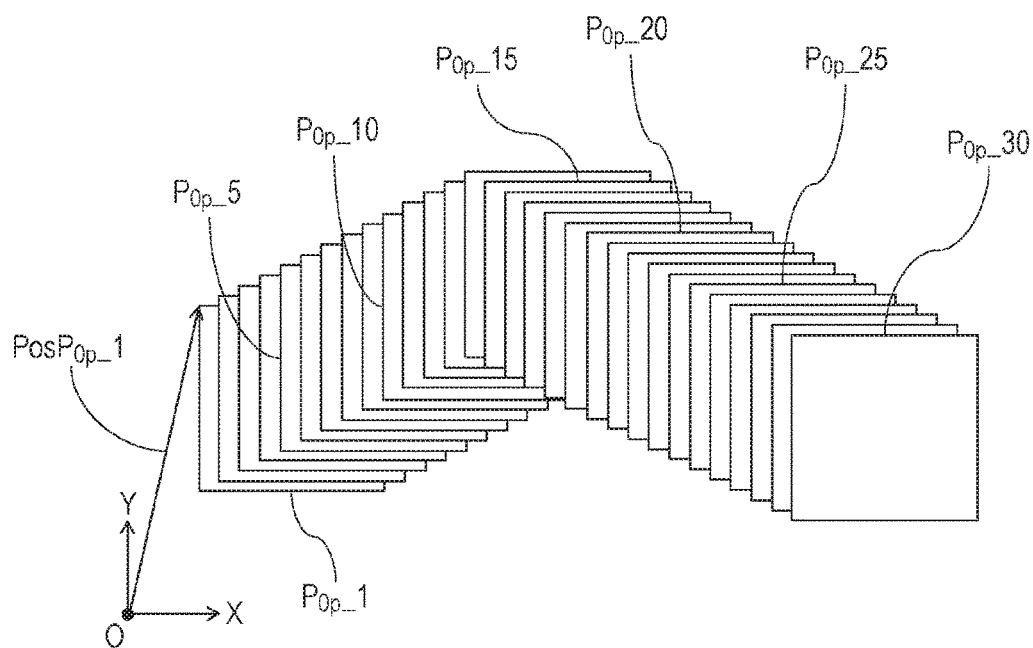
[Fig. 5]
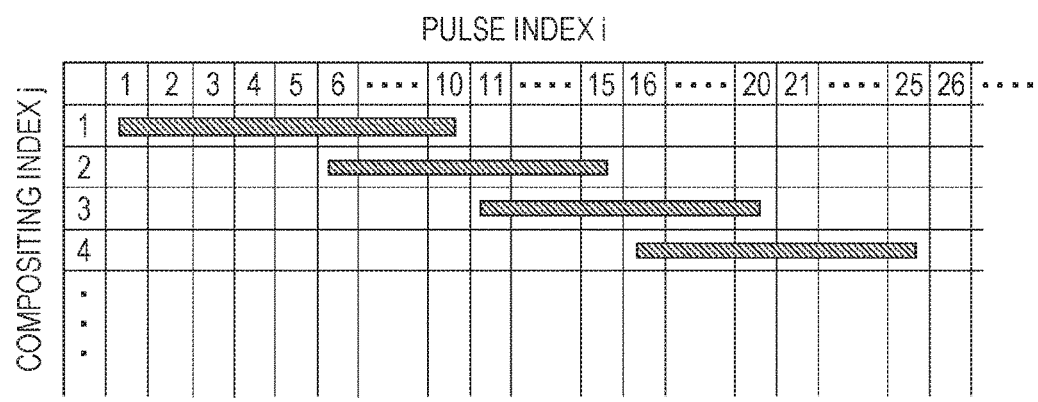

[Fig. 6A]
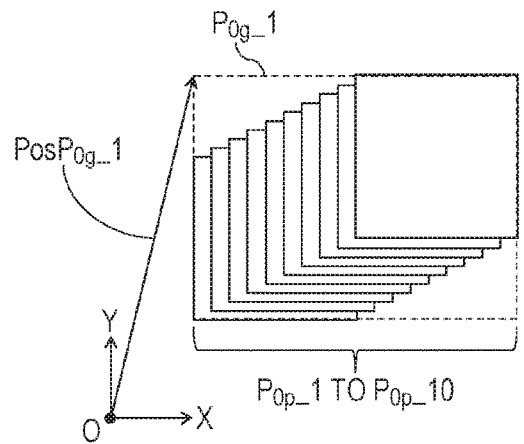
[Fig. 6B]
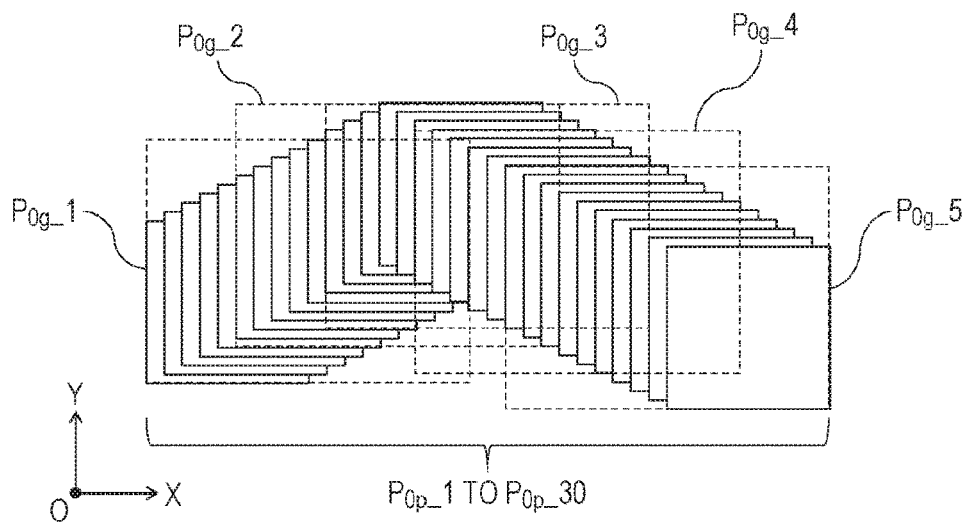
[Fig. 6C]
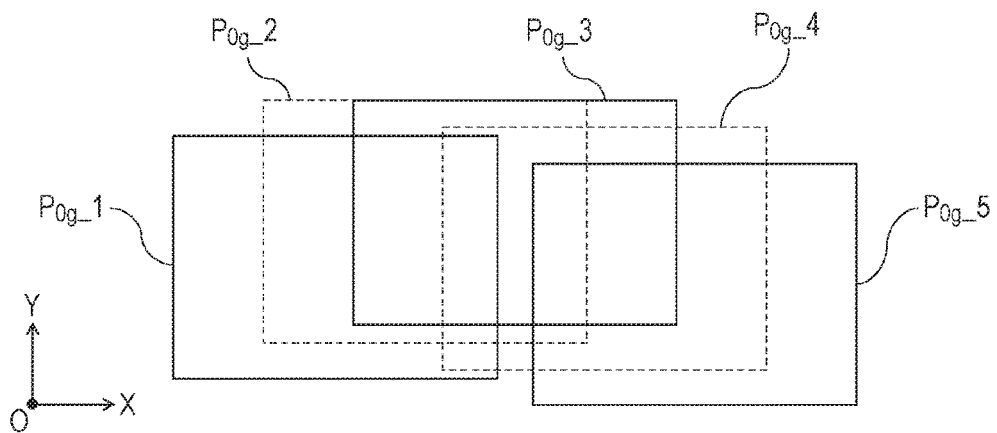

[Fig. 7]
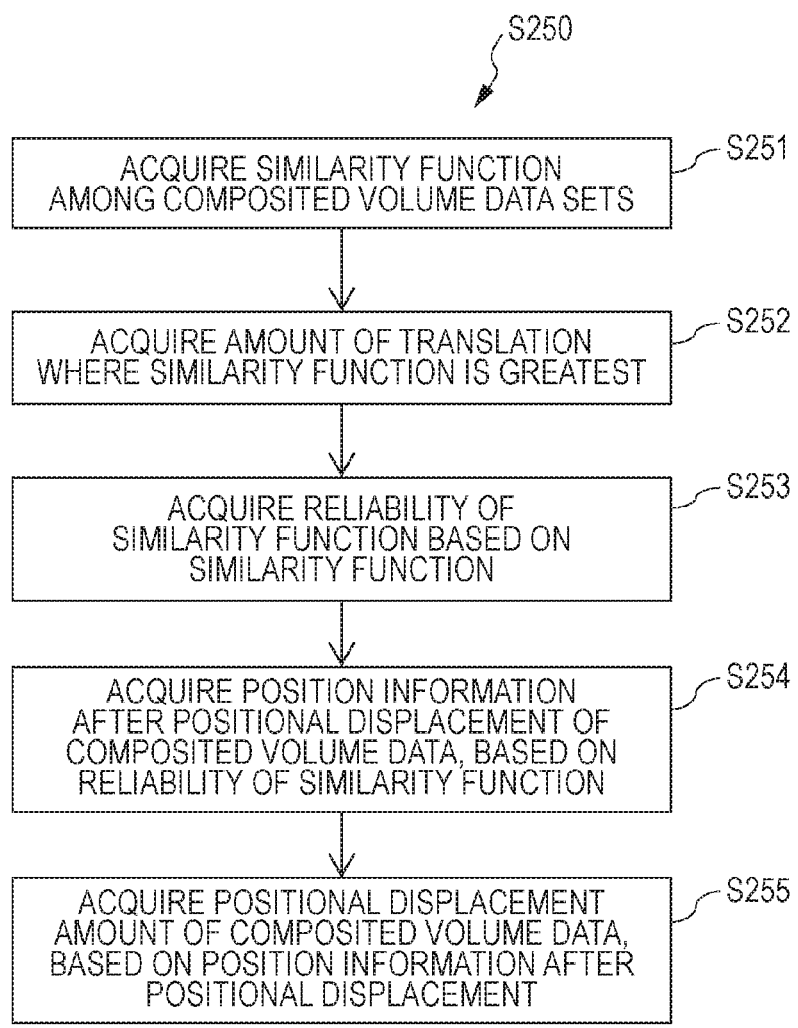

[Fig. 8]
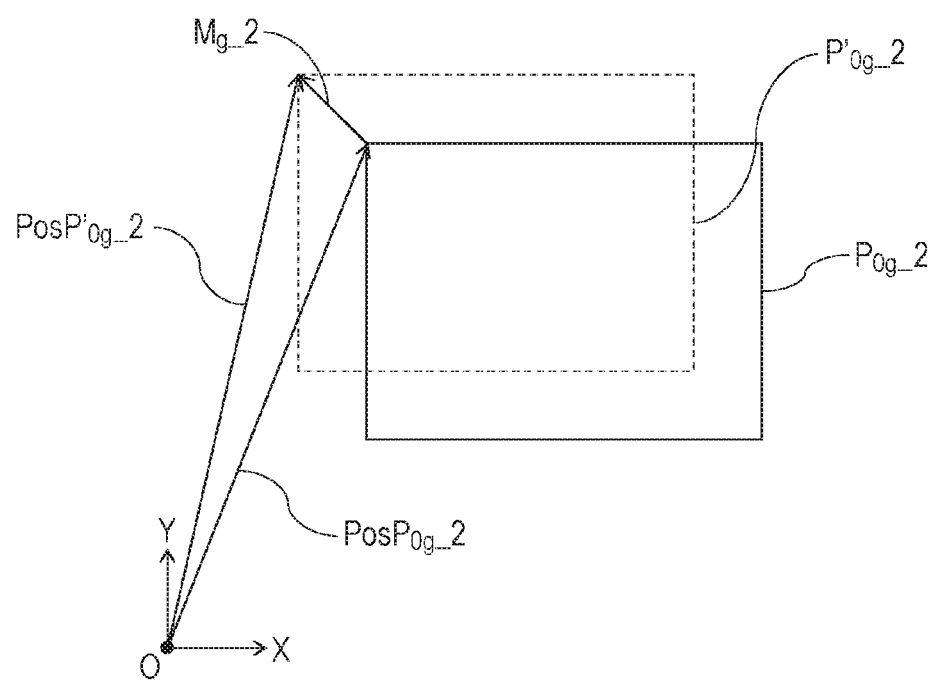

[Fig. 9A]
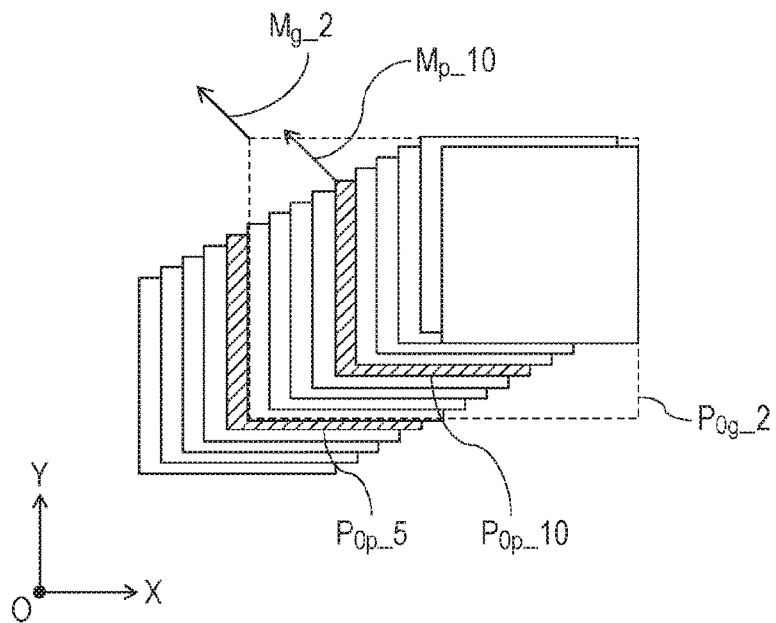
[Fig. 9B]
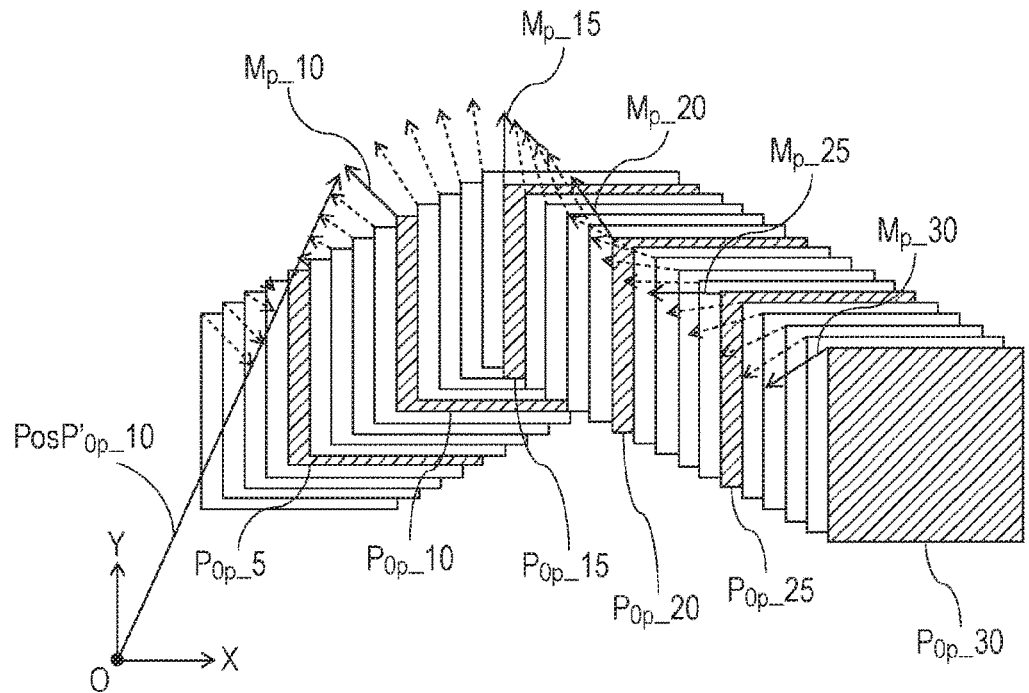

[Fig. 10A]
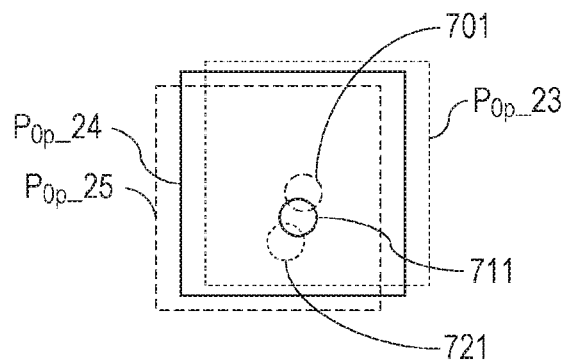
[Fig. 10B]
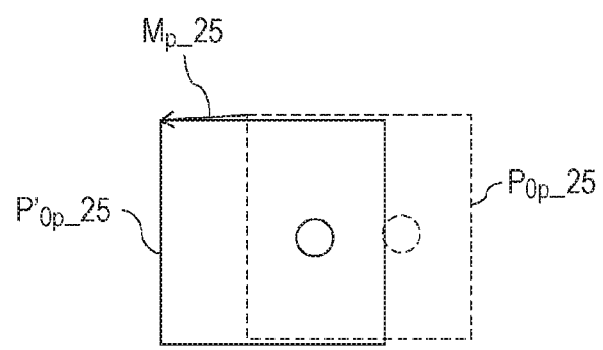
[Fig. 10C]
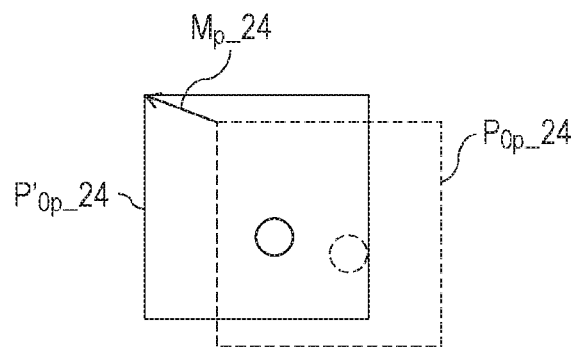

[Fig. 10D]
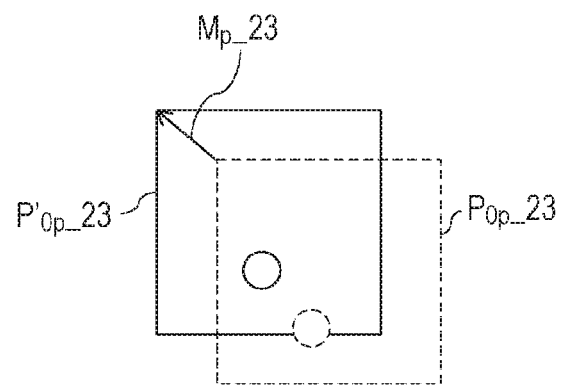
[Fig. 10E]
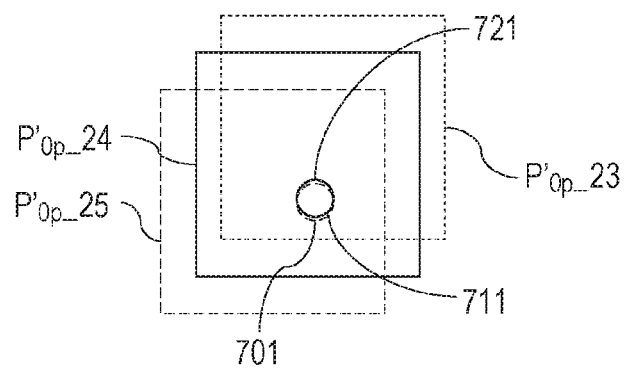

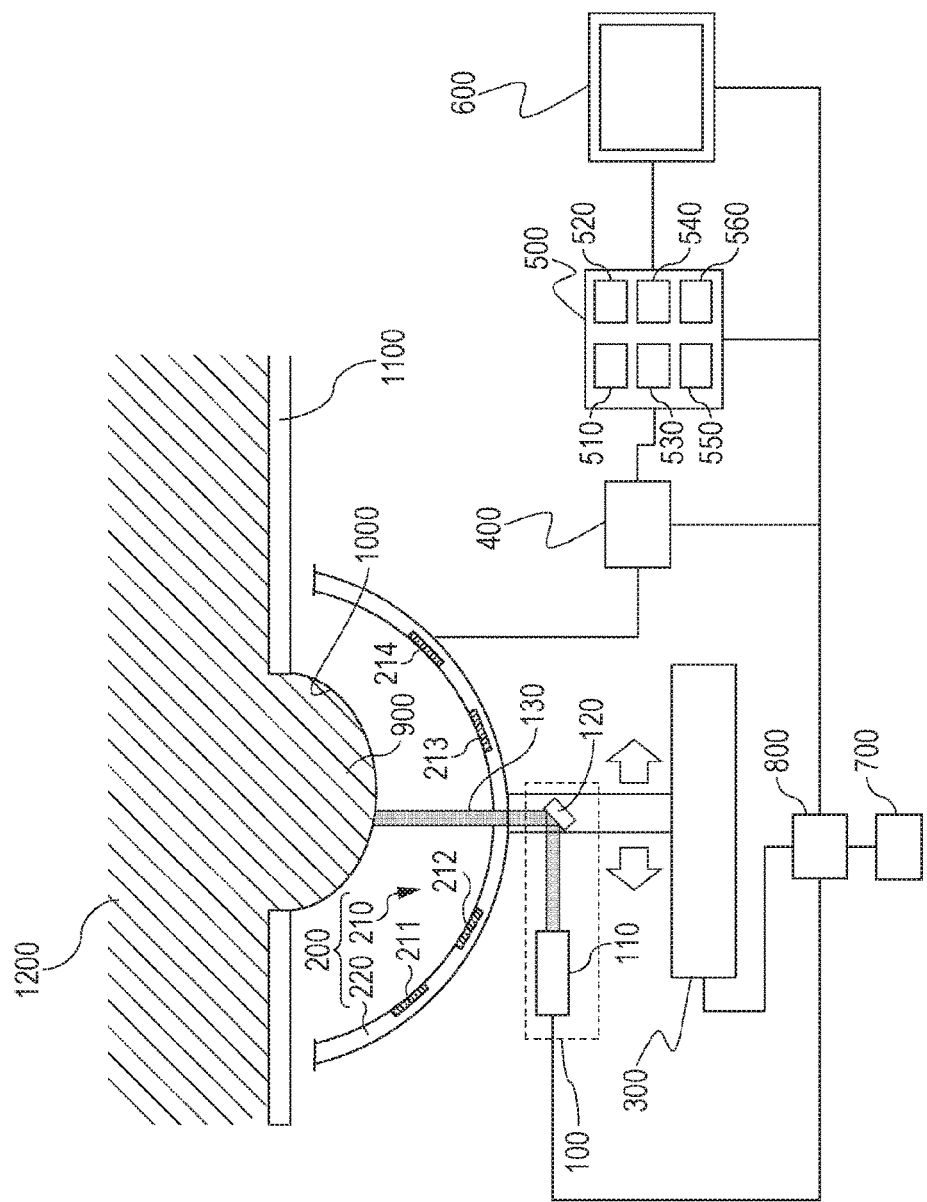
[Fig. 11]

[Fig. 12]
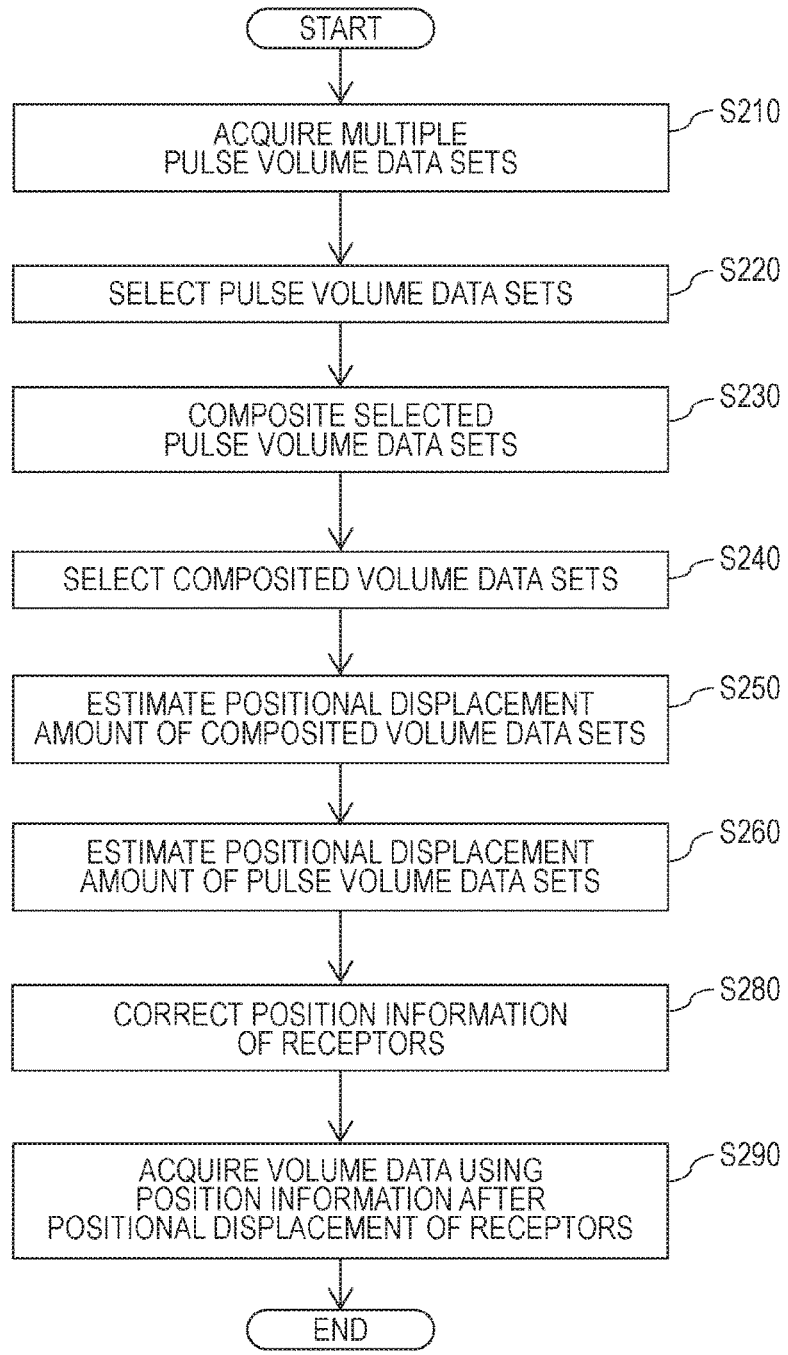

DEVICE FOR ACQUIRING INFORMATION RELATING TO POSITION DISPLACEMENT OF MULTIPLE IMAGE DATA SETS, METHOD, AND PROGRAM

TECHNICAL FIELD

The present invention relates to technology for acquiring information relating to position displacement of multiple image data sets.

BACKGROUND ART

Photoacoustic imaging technology is being studied, where an object is irradiated by light, and image data of the object is acquired using acoustic waves (photoacoustic waves) emitted by the photoacoustic effect, due to energy of the light being absorbed. There is a technique in photoacoustic imaging where image data sets of an object acquired by multiple irradiations of light are composited.

However, there is a possibility that the relative positional relationship between the object and the photoacoustic wave reception unit may change from one light irradiation to another. This causes positional displacement due to the change in the image data corresponding to each light irradiation. The result is that image data sets of the object that include positional displacement are composited with each other, and the quality of the composited image data sets of the object is lower. There is known a technique that addresses this problem by comparing the image data sets with each other, thereby estimating and correcting the positional displacement of the image data sets.

PTL 1 discloses estimating positional displacement amount by comparing the image data sets of the object with each other, and compositing the image data sets of the object after the positional displacement has been corrected. However, there is demand for further improvement in estimation precision regarding the positional displacement estimation method according to PTL 1.

CITATION LIST

Patent Literature

PTL 1: Japanese Patent Laid-Open No. 2014-140716

Non Patent Literature

NPL 1: Physical Review E 71, 016706 (2005)
NPL 2: Proc. of SPIE Vol. 7561 756117-1

SUMMARY OF INVENTION

The present invention provides a technology that improves the estimation precision of positional displacement amount of multiple image data sets, using multiple image data sets.

An apparatus according to the present invention includes: a first acquisition unit configured to acquire a first plurality of image data sets; a second acquisition unit configured to acquire first composited image data using a first two or more image data sets of the first plurality of image data sets; a third acquisition unit configured to acquire second composited image data, using a second two or more image data sets of the first plurality of image data sets, the second two or more image data sets being a combination different from the first two or more image data sets; a fourth acquisition unit configured to acquire information relating to positional displacement between the first composited image data and the second composited image data, using the first composited image data and the second composited image data; and a fifth acquisition unit configured to acquire information relating to the first plurality of image data sets, using information relating to the positional displacement between the first composited image data and the second composited image data.

An apparatus according to the present invention includes: a first acquisition unit configured to acquire a plurality of image data sets; a setting unit configured to set, from the plurality of image data sets, a plurality of pairs of image data; and a second acquisition unit configured to acquire, for each the plurality of pairs, a reliability of a similarity function representing the relationship between the relative position of the two image data sets making up the pair and the similarity of the two image data sets, and acquire information relating to positional displacement of the plurality of image data sets using the reliability of the similarity functions corresponding to the plurality of pairs.

Further features of the present invention will become apparent from the following description of exemplary embodiments with reference to the attached drawings.

BRIEF DESCRIPTION OF DRAWINGS

FIG. 1 is a diagram illustrating a photoacoustic device according to a first embodiment.

FIG. 2 is a diagram illustrating positions of a receiving unit at each of light irradiations according to the first embodiment.

FIG. 3 is a flowchart illustrating a processing flow at an image data acquisition unit according to the first embodiment.

FIG. 4 is a diagram illustrating pulse volume data sets according to first embodiment.

FIG. 5 is a diagram illustrating pulse volume data sets to be composited according to the first embodiment.

FIG. 6A is a diagram illustrating composited volume data sets according to the first embodiment.

FIG. 6B is a diagram illustrating composited volume data sets according to the first embodiment.

FIG. 6C is a diagram illustrating composited volume data sets according to the first embodiment.

FIG. 7 is a flowchart illustrating a positional displacement amount acquisition flow according to the first embodiment.

FIG. 8 is a diagram illustrating positional displacement amount of composited volume data sets according to the first embodiment.

FIG. 9A is a diagram illustrating positional displacement amount of pulse volume data sets according to the first embodiment.

FIG. 9B is a diagram illustrating positional displacement amount of pulse volume data sets according to the first embodiment.

FIG. 10A is a diagram for describing positional displacement correction processing of pulse volume data sets according to the first embodiment.

FIG. 10B is a diagram for describing positional displacement correction processing of pulse volume data sets according to the first embodiment.

FIG. 10C is a diagram for describing positional displacement correction processing of pulse volume data sets according to the first embodiment.

FIG. 10D is a diagram for describing positional displacement correction processing of pulse volume data sets according to the first embodiment.

FIG. 10E is a diagram for describing positional displacement correction processing of pulse volume data sets according to the first embodiment.

FIG. 11 is a diagram illustrating a different configuration of a photoacoustic device according to the first embodiment.

FIG. 12 is a different processing flowchart according to the first embodiment.

DESCRIPTION OF EMBODIMENTS

In photoacoustic imaging, there is a possibility that the relative positional relationship between the object and the photoacoustic wave reception unit may change from one light irradiation to another. This causes positional displacement due to the change in the image data corresponding to each light irradiation. The result is that image data sets of the object that include positional displacement are composited with each other, and the quality of the composited image data sets of the object is lower. There is known a technique that addresses this problem by comparing the image data sets with each other, thereby estimating and correcting the positional displacement of the image data sets.

However, sound pressure generated by photoacoustic waves is typically weaker as compared to sound pressure of transmission acoustic waves used in ultrasound diagnosis apparatuses. Accordingly, the signal-to-noise (hereinafter "S/N") ratio of image data of the object obtained by one light irradiation is lower than the S/N ratio of image data acquired by an ultrasound diagnosis apparatus that transmits and receives ultrasound. As a result, the precision of estimation of the positional displacement amount among image data sets, obtained by comparing image data sets of the object acquired from one light irradiation with each other, is poor. PTL 1 discloses estimating positional displacement amount with high precision by comparing image data sets of the object acquired by multiple light irradiations with each other, and compositing the image data sets of the object after the positional displacement has been corrected.

However, there is a possibility that the relative positional relationship between the object and the photoacoustic wave reception unit may change among the multiple light irradiations to acquire one image data set of an object in PTL 1 as well. There is a possibility that lower image quality due to this change will occur in the image data of the one image data set of the object acquired by multiple light irradiations as well. Accordingly, it is difficult to suppress lower quality due to the change occurring among multiple light irradiations to acquire one image data set of an object using the method disclosed in PTL 1.

A photoacoustic imaging technique will be described in the following embodiments where, even in a case where the relative positional relationship between an object and reception unit of photoacoustic waves changes during multiple times of performing irradiation by light, image data of the object can be acquired with the effects of this change having been suppressed.

The present invention will be described in greater detail with reference to the drawings. Note that the same components are denoted by the same reference numerals as a rule, and redundant description is omitted.

First Embodiment

A photoacoustic apparatus according to the present embodiment will be described with reference to FIG. 1. The photoacoustic apparatus according to the present embodiment includes a light irradiation unit 100, a reception unit 200, a driving unit 300, a signal collecting unit 400, an image data acquisition unit 500, display unit 600, an input unit 700, and a control unit 800. Configurations of the photoacoustic apparatus according to the present embodiment will be described below.

Light Irradiation Unit 100

The light irradiation unit 100 includes a light source 110, and an optical system 120 that guides light emitted from the light source 110 to an object 900. The light source 110 may be a laser, light emitting diode, or the like. A wide variety of lasers can be used, including solid-state laser, gas laser, dye laser, semiconductor laser, and so forth. Pulsed lasers such as Nd:YAG laser, alexandrite laser, or the like may be used as the light source 110. Further, Ti:sapphire laser that uses Nd:YAG laser as excitation light or optical parametric oscillator (OPO) laser may be used as the light source 110.

The light source 110 may be a pulsed light source that is capable of generating pulsed light in the order of nanoseconds to microseconds. The pulse width of the light may be around 1 to 100 nanoseconds. The wavelength of the light may be in a range of around 400 nm to 1600 nm. In a case of high-resolution imaging of blood vessels in the vicinity of a biological surface, light of a wavelength may be used where absorption by blood vessels is great (400 nm or higher, 700 nm or lower). On the other hand, in a case of imaging at deep parts of biological tissue, light of a wavelength may be used where absorption by background tissue (water, fat, etc.) is typically low (700 nm or higher, 1100 nm or lower). In a case of irradiating the object by multiple wavelengths, a light source may be sued where wavelength conversion can be performed. Note that multiple light sources that generate light of different wavelengths from each other may be prepared, and the object irradiated by these light sources in an alternating manner. In a case where multiple light sources are used, these will be collectively referred to as "light source".

Optical elements such as lenses, mirrors, optical fiber, and so forth, can be used for the optical system 120. The light emission portion of the optical system 120 may be configured using a diffuser plate to diffuse light, so that irradiation is performed with a wider light beam diameter. On the other hand, in photoacoustic microscopy, the light emission portion of the optical system 120 may be configured using a lens or the like to raise resolution, and irradiation may be performed by focusing the beam. Note that an arrangement may be made where the light irradiation unit 100 does not have the optical system 120, and the object 900 is directly irradiated by light from the light source 110.

Reception Unit 200

The reception unit 200 includes a receptor group 210 made up of receptors 211 through 214 that output electrical signals by receiving photoacoustic waves, and a supporting member 220 that supports the receptor group 210.

Materials that can be used to make up the receptors 211 through 214 include piezoelectric ceramic materials of which lead zirconate titanate (PZT) is representative, polymeric piezoelectric membrane materials of which polyvinylidene fluoride (PVDF) is representative, and so forth. For examples, capacitive micromachined ultrasonic transducers (CMUT), transducers using Fabry-Perot interferometers, and so forth, can be used. Note that any transducer can be employed as a receptor, as long as electric signals can be output by receiving acoustic waves.

The supporting member 220 is preferably configured using a metal material with high mechanical strength. The supporting member 220 in the present embodiment has the shape of a half-sphere shell, configured so that the receptor group 210 can be supported on the half-sphere shell. In this case, the axes of orientation of the receptors are converged around the center of curvature of the half-sphere. The image quality also is higher near the center of curvature when imaging is performed using the electric signal group output from these receptors. Note that the supporting member 220 may have any configuration as long as it is capable of supporting the receptor group 210.

Driving Unit 300

The driving unit 300 is a device that changes the relative position between the object 900 and the reception unit 200. The driving unit 300 in the present embodiment is a device that moves the supporting member 220 in the X-Y direction, and is an electric-powered XY stage equipped with a stepping motor.

The driving unit 300 includes a motor such as a stepping motor to generate driving force, a driving mechanism that transmits driving force, and a position sensor that detects positional information of the reception unit 200. A lead screw mechanism, link mechanism, gear mechanism, hydraulic mechanism, or the like, may be used for the driving mechanism. The position sensor may use a potentiometer or the like employing an encoder, variable resistor, or the like.

Note that the driving unit 300 is not restricted to changing the relative position between the object 900 and the reception unit 200 in the X-Y direction (two dimensionally), and may change the relative position one dimensionally or three dimensionally.

Note that the driving unit 300 may fix the reception unit 200 and move the object 900, as long as the relative position between the object 900 and the reception unit 200 can be changed. In a case of moving the object 900, a configuration is conceivable where the object 900 is moved by moving an object supporting unit (omitted from illustration) that supports the object 900. Alternatively, both the object 900 and the reception unit 200 may be moved.

The driving unit 300 may continuously move the relative position, or may move the relative position by step-and-repeat. The driving unit 300 preferably is an electric powered stage, but may be a manual stage.

Signal Collecting Unit 400

The signal collecting unit 400 includes an amplifier that amplifies electrical signals that are analog signals output from the receptors 211 through 214, and an A/D converter that converts analog signals output from the amplifier into digital signals (both amplifier and A/D converter are omitted from illustration). The digital signals output from the signal collecting unit 400 are stored in a storage unit 510 within the image data acquisition unit 500. The signal collecting unit 400 is also referred to as a data acquisition system (DAS). In the present specification, "electrical signals" is a concept including both analog signals and digital signals.

Image Data Acquisition Unit 500

The image data acquisition unit 500 is a device that stores the digital signals output from the signal collecting unit 400, and acquires image data of the object 900 based on the stored digital signals. Details of the processing performed by the image data acquisition unit 500 will be described later.

"Image data" as used in the present embodiment is a collective term for information at each position in two-dimensional or three-dimensional space that is obtained based on an electric signal group, acquired by receiving photoacoustic waves generated by the photoacoustic effect. Specifically, image data is relating to generated sound pressure (initial sound pressure) of photoacoustic waves (expressed in units of Pa), light energy absorption density, (expressed in units of J/m$^3$), light absorption coefficient (expressed in units of 1/m), information relating to density of matter making up the object, and so forth. The information relating to density of matter is oxyhemoglobin density, deoxyhemoglobin density, total hemoglobin density, degree of oxygen saturation, and so forth. Total hemoglobin density is the sum of oxyhemoglobin density and deoxyhemoglobin density. The degree of oxygen saturation is the rate of oxyhemoglobin as to all hemoglobin.

The image data acquisition unit 500 includes the storage unit 510, a reconstruction unit 520, a selecting unit 530, a compositing unit 540, a projection data acquisition unit 550, and a position estimation unit 560. The storage unit 510 may be configured using a non-transitory storage medium such as a magnetic disk or flash memory or the like. The storage unit 510 may also be a volatile medium such as dynamic random access memory (DRAM) or the like. Note that the storage medium where the program is stored is a non-transitory storage medium.

A unit handling the computation functions of the reconstruction unit 520, selecting unit 530, compositing unit 540, projection data acquisition unit 550, and position estimation unit 560 may be configured using a processor such as a central processing unit (CPU) or graphics processing unit (GPU) or the like, a computation circuit such as a field programmable gate array (FPGA) chip, or the like. These units are not restricted to being configured as a single processor or computation circuit, and may be configured as multiple processors or computation circuits.

Display Unit 600

The display unit 600 is a display such as a liquid crystal display, an organic electroluminescence (EL) display, or the like, serving as a device to display images based on image data acquired from the image data acquisition unit 500, numeric values at a predetermined position within the image data, and so forth. The display unit 600 may display a user interface (UI) for operation of images and devices. The display unit 600 may be provided separately from the photoacoustic apparatus.

Input Unit 700

The input unit 700 may be configured using a mouse, keyboard, touch panel, or the like, that the user can operate. Note that the input unit 700 may be provided separately from the photoacoustic apparatus.

Control Unit 800

The control unit 800 receives signals due to various types of operations, such as to start imaging or the like, from the input unit 700 and controls various configurations of the photoacoustic apparatus. The control unit 800 reads out programs stored in the storage unit, and controls operations of the configurations of the photoacoustic apparatus. The control unit 800 is configured using a computing element such as a CPU or the like.

Note that the configurations of the photoacoustic apparatus may be each configured as separate devices, or may be integrally configured as a single device. Also, multiple configurations of the photoacoustic apparatus may be integrally configured as a single device.

The following is a description of operations of the photoacoustic apparatus according to the present embodiment. The light irradiation unit 100 repeatedly irradiates the object 900 with a 20 Hz repetition frequency of light 130. Acoustic waves (photoacoustic waves) are generated within the object 900 from the photoacoustic effect due to the light 130. The resonators 211 through 214 receive the photoacoustic waves and output electric signals, whereby the reception unit 200 outputs an electric signal group. The electric signals output from the receptors are time-sequence signals indicating the temporal change in pressure of the photoacoustic waves that have reached each of the receptors.

The driving unit 300 moves the reception unit 200, while the light irradiation unit 100 irradiates the object 900 with light multiple times. That is to say, the driving unit 300 moves the reception unit 200 during a period over which light irradiation is performed multiple times. As a result, the driving unit 300 can move the reception unit 200 so that the reception unit 200 is at different positions each time irradiation by light is performed. FIG. 2 represents an example of the positions of the reception unit 200 at the times of irradiation by light. The points in FIG. 2 have been plotted at positions of the base of the supporting member 220 at the times of irradiation by light. The light irradiation unit 100 performs irradiation by light N times, and the reception unit 200 receives photoacoustic waves at N positions. The number of times of irradiation by light is 2050 times in FIG. 2, and the average movement distance of the reception unit 200 at time intervals between irradiation by light is approximately 1.5 mm.

The receptor group 210 receives the photoacoustic waves generated by multiple irradiations of light by the light irradiation unit 100, thereby output multiple electrical signal groups corresponding to each of the multiple irradiations of light. That is to say, the receptor group 210 outputs as many electrical signal groups as the number of irradiations by light by the light irradiation unit 100. Hereinafter, the multiple electrical signal groups corresponding to the respective multiple irradiations by light will be referred to simply as "electrical signal group".

A case of performing irradiation by light N times will be described below. A received signal group obtained by irradiation by light the i'th time will be written as $P_{dp\_}i$ (i is no smaller than 1 and no larger than N). Items with the suffix "i" are items corresponding to the i'th irradiation by light. This i is a positive integer, and is also referred to as a "pulse index". Items with a suffix "p" are items corresponding to the first irradiation by light.

The signal collecting unit 400 converts the multiple electrical signal groups, that are the analog signal groups output from the receptor group 210, into digital signal groups, to be stored in the storage unit 510.

The image data acquisition unit 500 acquires image data of the object, based on the multiple electrical signal groups stored in the storage unit 510. The image data acquisition unit 500 transmits the image data of the object to the display unit 600, so as to display images based on image data, numeric values at a predetermined position within the image data, and so forth. In a case where the image data is three-dimensional, the image data acquisition unit 500 can display a tomographic image cut away at any cross-section, a maximum intensity projection (MTP) image, an image subjected to volume rendering, or the like.

Hereinafter, processing of the image data acquisition unit 500 acquiring image data of an object will be described in detail with reference to the processing flowchart illustrated in FIG. 3.

<S210: Process of Acquiring Multiple Pulse Volume Data Sets>

The reconstruction unit 520 acquires multiple image data sets of the object, each corresponding to the multiple irradiations by light, based on each electrical signal group of the multiple electrical signal groups stored in the storage unit 510. That is to say, the reconstruction unit 520 converts the electrical signal groups that represent temporal change of pressure into image data of the object. Image data acquired by one irradiation by light will also be referred to as a pulse volume data set. Pulse volume data is acquired in a volume data format where values are stored at respective positions of voxels (also called pixels if two-dimensional) arrayed two-dimensionally or three-dimensionally. Volume data can also be referred to as two-dimensional or three-dimensional volume, two-dimensional or three-dimensional image, or two-dimensional or three-dimensional tomographic image.

In the present embodiment, the reconstruction unit 520 acquires multiple initial sound pressure distribution data $P_{Op\_}i$ sets, corresponding to each of the multiple irradiations by light, based on each electrical signal group of the multiple electrical signal groups stored in the storage unit 510. The multiple initial sound pressure distribution data $P_{Op\_}i$ sets are stored in the storage unit 510. A case of acquiring three-dimensional spatial distribution information of initial sound pressure as image data of the object will be described in the present embodiment. The value of the initial sound pressure distribution data at each position is described by a function expression such as $P_{Op\_}i(x, y, z)$. Hereinafter, the multiple initial sound pressure distribution data $P_{Op\_}i$ sets corresponding to each of the multiple irradiations by light may also be referred to simply as multiple initial sound pressure distribution data sets.

Known reconstruction techniques such as a time domain reconstruction technique, Fourier domain reconstruction technique, model-based reconstruction technique (iterative reconstruction technique), and the like can be employed for the reconstruction technique. For example, a time domain reconstruction technique called Universal Back Projection (UBP) described in NPL 1 can be employed.

In addition to the multiple electrical signal groups, the reconstruction unit 520 also acquires multiple initial sound pressure distribution data sets based on position information of the receptors at each irradiation by light. The reconstruction unit 520 can acquire the position information by reading out position information of each receptor at each irradiation by light stored in the storage unit 510 beforehand. The reconstruction unit 520 can also acquire the position information of each receptor by receiving the position information of the reception unit 200 from a position sensor provided to the driving unit 300, with the irradiation by light as a trigger.

FIG. 4 illustrates a portion of pulse volume data sets ($P_{Op\_}1$ through $P_{Op\_}30$) according to the present embodiment. Although the pulse volume data according to the present embodiment is volume data in three-dimensional space, the pulse volume data is represented by an X-Y plane for the sake of convenience in description on paper. In the present embodiment, a reconstruction region is set so that temporally-adjacent initial sound pressure distribution data sets are superimposed at least partially. A cubic region that is 60 mm in each direction, and centered on the center of curvature of the supporting member 220 of the half-sphere, is used as the reconstruction region in the present embodiment to be reconstructed based on one irradiation by light, i.e., one electrical signal group. In this case, the size (60 mm) of the reconstruction region is large as compared to the amount of movement (1.5 mm) of the reception unit 200 in the time interval between irradiations by light. Accordingly, two or more pulse volume data sets that correspond to temporally-consecutive irradiations by light are superimposed, as illustrated in FIG. 4. The size and shape of the reconstruction region can be set beforehand. Alternatively, the user may specify the size and shape of the reconstruction region by using the input unit 700. A position at the upper left edge of each pulse volume data set in the drawing as to a reference position O is the position of each pulse volume data set. As an example, the position $\text{PosP}_{Op\_}1$ of the pulse volume data set $P_{Op\_}1$ is illustrated in FIG. 4. The position of the reception unit 200 differs for each irradiation by light, as illustrated in FIG. 2, so each pulse volume data set obtained in the present embodiment that is illustrated in FIG. 4 is positioned at a different position from each other as to the reference position O. That is to say, in the present embodiment, the positions of the pulse volume data sets are decided by the position of the reception unit 200 at the time of irradiation by light. Note that the position information of the reception unit 200 at the time of irradiation by light may be acquired, and the positions of the acquired pulse volume data sets be decided, based on this position information. Alternatively, the positions of the pulse volume data sets may be decided based on the positions of irradiation by light. Further, the positions of the pulse volume data sets acquired in this process may be set beforehand.

Note that in this process, the reconstruction unit 520 may acquire light fluence distribution data $\Phi(\text{J/m}^2)$ within the object, and Gruneisen coefficient distribution data $\Gamma(\text{Pa}\times\text{m}^3/\text{J})$ within the object. The reconstruction unit 520 may then acquire light absorption coefficient distribution data $\mu_a$ (1/m) by dividing the initial sound pressure distribution data by the light fluence distribution data and Gruneisen coefficient distribution data. In this case, the light absorption coefficient distribution data can be taken as the pulse volume data.

For example, the reconstruction unit 520 may acquire the light fluence distribution data by solving a light diffusion equation as described in NPL 2.

It is known that the value of the Gruneisen coefficient is almost uniquely determined when the type of object is determined, so for example, the Gruneisen coefficient distribution data $\Gamma$ can be stored in the storage unit 510 beforehand. The reconstruction unit 520 then may perform acquisition by reading out the Gruneisen coefficient distribution data $\Gamma$ stored in the storage unit 510.

Note that the reception unit 200 may have a grasping portion, and the user may grasp the grasping portion so as to move the reception unit 200. Alternatively, an arrangement may be made where the reception unit 200 is not moved during the multiple irradiations by light. The reconstruction unit 520 may also acquire image data for the entire imaging region based on an electrical signal group obtained by one irradiation by light, and repeat this for multiple irradiations by light.

<S220: Process of Selecting Pulse Volume Data>

The selecting unit 530 selects two or more pulse volume data sets corresponding to temporally-consecutive irradiations by light, out of the multiple pulse volume data sets stored in the storage unit 510. The two or more pulse volume data sets selected here will be collectively referred to as first group data $G_{g\_}1$.

The selecting unit 530 selects two or more pulse volume data sets corresponding to temporally-consecutive irradiations by light, regarding which the combination of the pulse volume data sets is different from the first group data and also includes part of the pulse volume data sets included in the first group data. The two or more pulse volume data sets selected here will be collectively referred to as second group data $G_{g\_}2$.

The j'th group data is written as $G_{g\_}j$ (j is no smaller than 1 and no larger than M) in the present specification. An item with the suffix j indicates that this is an item corresponding to the j'th group data. This j is a positive integer, and is also referred to as a group index. An item with the suffix g indicates that this is an item corresponding to one group data.

FIG. 5 indicates an example of selecting pulse volume data sets in the present embodiment. The selecting unit 530 selects ten initial sound pressure distribution data sets $P_{Op\_}1$ through $P_{Op\_}10$ corresponding to the first through tenth irradiations by light as the first group data $G_{g\_}1$. The selecting unit 530 also selects ten initial sound pressure distribution data sets $P_{Op\_}6$ through $P_{Op\_}15$ corresponding to the sixth through fifteenth irradiations by light as the second group data $G_{g\_}2$. Here, in each group data, the initial sound pressure distribution data sets corresponding to the sixth through tenth irradiations by light are selected as common initial sound pressure distribution data to both of the group data. In the same way, a plurality of group data $G_{g\_}1$ through $G_{g\_}M$ can be selected by performing selection by shifting the ten initial sound pressure distribution data sets corresponding to the ten irradiations by light that are selected, by five irradiations by light at a time, that is to say, the group data $G\_j$ includes the initial sound pressure distribution data $P_{Op\_}(5j-4)$ through $P_{Og\_}(5j+5)$ In the case of the present embodiment, one group data is configured of ten electrical signal groups, and a plurality of group data is formed by shifting five electrical signal groups at a time. Accordingly, the number (M) of composited volume data is smaller than the number (N) of pulse volume data.

Note that the selecting unit 530 may select the pulse volume data based on the image quality of each pulse volume. The selecting unit 530 may select the pulse volume data so that the selected pulse volume data has a predetermined quality or higher when composited. The selecting unit 530 may select a smaller number of pulse volume data sets of high image quality as compared to pulse volume data sets of low image quality, as one group. Image quality as used here means signal level, S/N, contrast, or the like, in the volume data. For example, a case will be assumed in this pulse volume data where strong intensity values are observed in a region where a part of a subject taken has generated strong photoacoustic waves, and weak intensity values are observed at other regions. The selecting unit 530 may also calculate the average of luminance values within this pulse volume data, or calculate signal levels based on variance of luminance values, or the like. Further, an arrangement may be made where the selecting unit 530 calculates the ratio between components from photoacoustic waves and noise components, based on the luminance values of the pulse volume data, and calculate the S/N based on this. In this case, for example, the selecting unit 530 performs spatial frequency analysis regarding the luminance values of this pulse volume data. The selecting unit 530 may then take components of luminance values having a predetermined frequency or higher as noise, and components of luminance values of frequencies lower than this as components based on photoacoustic waves, thereby calculating the S/N according to the ratio of these components. Thus, the number of pulses to be composited can be adaptively changed in accordance with the image quality of each pulse volume data set. Accordingly, volume data can be generated where the image quality is at or higher than a predetermined level.

In a case where thesis of the object and the change in body movement is known, the selecting unit 530 may select pulse volume data sets based on the magnitude of body movement. Specifically, the selecting unit 530 may reduce the number of pulses to be selected when the body movement is large, and increase the number of pulses to be selected when the body movement is small. Accordingly, when the body movement of the subject is large, fewer pulse volume data sets are composited in the later-described S230. This can suppress blurring in the composited volume data due to the effects of body movement. On the other hand, when the body movement of the subject is small, more pulse volume data sets are composited in the later-described S230. This has the advantage that volume data can be composited with the effects of noise included in the pulse volume data having been reduced.

The selected pulse volume data sets are composited, as described later. The positional displacement among the selected pulse volume data sets preferably is small, to suppress blurring of the volume data after compositing. Accordingly, pulse volume data sets corresponding to two or more irradiations by light may be selected from irradiations by light performed within a predetermined period. The predetermined period corresponding to the first group data will be referred to as first period, and the predetermined period corresponding to the second group data will be referred to as second period. The predetermined periods are decided according to the magnitude of positional displacement and cycle. For example, pulse volume data sets may be selected that are included in a period corresponding to ¼ cycle of positional displacement. In a case of assuming positional displacement due to breathing, pulse volume data sets included within one second may be selected. In a case of assuming positional displacement due to relatively fast breathing, pulse volume data sets included within 0.5 seconds may be selected. Any combination of pulse volume data sets may be selected, as long as the pulse volume data sets are selected within a predetermined period. That is to say, the selected pulse volume data sets do not have to be temporally consecutive.

<S230: Process of Compositing Selected Pulse Volume Data Sets>

The compositing unit 540 acquires composited volume data by compositing the two or more pulse volume data sets selected in S220.

The compositing unit 540 in the present embodiment composites the initial sound pressure distribution data sets $P_{Op\_}1$ through $P_{Op\_}10$ included in the first group data $G_{g\_}1$ selected by the selecting unit 530, thereby acquiring an initial sound pressure distribution data set $P_{Og\_}1$. The first composited initial sound pressure distribution data is equivalent to the first composited volume data (first composited image data). The compositing performed to acquire the first composited volume data will be referred to as first compositing.

FIG. 6A illustrates the first composited volume data $P_{Og\_}1$ acquired by the first compositing. In the present embodiment, a region that envelops all of pulse volume data sets $P_{Op\_}1$ through $P_{Op\_}10$ to be composited and also is a minimally small rectangular region is taken as the first composited volume data $P_{Og\_}1$. Note that any region that envelops regions where at least two or more pulse volume data sets are superimposed may be taken as composited volume data. that is to say, the region of the composited volume data does not need to envelop all pulse volume data sets that are the object of compositing.

In the same way as with the pulse volume data sets, a position at the upper left edge in the drawing as to the reference position O is the position $PosP_{Og\_}1$ of the first volume data set.

The compositing unit 540 composites the initial sound pressure distribution data sets $P_{Op\_}6$ through $P_{Op\_}15$ included in the second group data selected by the selecting unit 530, and acquires the second composited second composited initial sound pressure distribution data $P_{Og\_}2$. The j'th composited initial sound pressure distribution data obtained by compositing the initial sound pressure distribution data included in the j'th group data is written as $P_{Og\_}j$. The second composited initial sound pressure distribution data is equivalent to the second composited volume data (second composited image data). The compositing performed to acquire the second composited volume data will be referred to as second compositing.

FIG. 6B illustrates composited volume data $P_{Og\_}1$ through $P_{Og\_}5$, obtained based on the pulse volume data sets $P_{Op\_}1$ through $P_{Op\_}30$ illustrated in FIG. 6A. The solid lines in FIG. 6B illustrate the pulse volume data sets, while the dashed lines indicate composited volume data sets.

FIG. 6C illustrates just the composited volume data sets $P_{Og\_1\ through\ }P_{Og\_}5$ illustrated in FIG. 6B. The solid lines in FIG. 6B illustrate the composited volume data sets $P_{Og\_}1$, $P_{Og\_}3$, and $P_{Og\_}5$, while the dashed lines indicate the composited volume data sets $P_{Og\_}2$ and $P_{Og\_}4$.

The compositing unit 540 in the present embodiment acquires composited volume data by performing averaging processing on the selected pulse volume data sets. This averaging processing (averaging) is performed by computation of adding the luminance values of each pulse volume regarding regions where the pulse volumes are superimposed, and dividing by the number of superimposed pulse volumes.

The compositing unit 540 may acquire weight volume data $Wg\_j(x, y, z)$ along with the composited volume data $P_{Og\_}j$. The weight volume data $Wg\_j$ is volume data representing the number of pulse volume data sets superimposed at each position in the composited volume data $P_{Og\_}j$ (in the case of performing averaging processing, the value to divide by). The value of the composited volume data is though to be high at positions where acquired by compositing a greater number of pulse volume data sets. That is to say, the weight volume data $Wg\_j$ is conceived to be a value that represents the reliability of the composited volume data at each position.

Note that the compositing position is not restricted to averaging processing, and that any technique may be used as long as volume data can be accrued that reproduces the features of the object more accurately as compared to a single pulse volume data set. Note however, the processing of correcting change in the relative position between the object 900 and the reception unit 200 during time intervals between irradiations by light (e.g., processing of changing the position of the pulse volume) is not included in "compositing" as used in the present specification.

For example, the compositing unit 540 may perform compositing by weighting each of the pulse volume data sets to be composited, and thereafter adding these. The compositing unit 540 may also calculate added values and average values for pulse volume data sets where values including much noise have been excluded by outlier exclusion or the like. Such compositing processing enables composited volume data to be obtained that accurately reproduces the features of the object, with noise included in the pulse volume data sets having been reduced.

By selecting pulse volume data sets that are temporally consecutive in S230 as described in the present embodiment, pulse volume data sets with little temporal change can be composited in this process. Thus, this process enables composited volume data to be acquired where the effects of change in relative position between the object and the reception unit of photoacoustic waves over multiple irradiations by light have been minimized.

Composited volume data with improved quality can be acquired by compositing multiple pulse volume data sets of which the quality of each is not high. However, the composited volume data acquired in this process includes the effects of change in relative position between the object and the reception unit of photoacoustic waves over multiple irradiations by light. Accordingly, there is a possibility that the quality of the composited volume data may be reduced due to the influence of this change. Processing to estimate the position of pulse volume data sets from estimated positions of the composited volume data, to suppress lowered quality, will be described next.

Note that the selecting unit 530 may reselect the pulse volume data sets to be composited, based on the image quality of the composited volume data acquired in this process. Specifically, in a case where the image quality of the composited volume data is lower than a predetermined image quality, the selecting unit 530 may add pulse volume data sets for compositing, and reselect. Accordingly, the composited volume data can be kept at a predetermined image quality or higher, so the estimation precision of the position of the composited volume data in the later-described S250 is improved. Also, the selecting unit 530 may reselect the pulse volume data sets to be composited in a case where the image quality of the composited volume data is higher than a predetermined image quality. Thus, the number of pulse volume data sets to attain a predetermined image quality or higher can be reduced, thereby suppressing inclusion of blurring in the composited volume data due to the effects of body movement.

The reconstruction unit 520 may acquire composited volume data based on two or more electrical signal groups acquired by irradiations by light corresponding to two or more pulse volume data sets selected in S220. In this case, the electrical signal groups may be selected in the same way as the method used for selecting the pulse volume data sets, described in S220. The reconstruction unit 520 may also generate one volume data set from two or more electrical signal groups without generating pulse volume data sets for each electrical signal groups. The reconstruction region size to be applied to one electrical signal group may be smaller than the entire imaging region, as described in S210. Alternatively, the reconstruction region size to be applied to one electrical signal group may be the same as the size of the entire imaging region. That is to say, the reconstruction unit 520 may apply each of the electrical signal groups to the entire imaging region.

<S240: Process of Selecting Composited Volume Data>

The position estimation unit 560 selects an optional pair of composited volume data sets from the multiple composited volume data sets acquired in S230. The k'th pair is written as R_k. One of the composited volume data sets making up the pair R_k is written as $P_{Og\_}k1$, and the other as $P_{Og\_}k2$. A case where K pairs are selected will be described in the present embodiment.

Note that two composited volume data sets having an overlapping region are preferably paired. This enables a situation where composited volume data sets not having any common features are compared in the later-described S250 to be avoided, so redundant calculation can be reduced. Pairing composited volume data sets with large overlapping regions is even more preferable. Accordingly, the position estimation unit 560 may select pairs where the volume of the overlapping regions among the composited volume data sets is a predetermined value or greater. Alternatively, for example, the position estimation unit 560 may select pairs where the percentage of volume of the overlapping region as to the composited volume data is a predetermined value or greater. Further, pairs may be selected where regions overlap that have a large number of superimposed pulse volume data sets within the composited volume data.

Alternatively, composited volume data sets having a group index included in a predetermined group index range from the group index of a certain composited volume data may be selected with regard to certain composited volume data. Or, composited volume data sets of which group indices are consecutive, i.e., temporally consecutive, may be selected to be paired.

For example, the position estimation unit 560 in the present embodiment selects, as an object for compositing with $P_{Og\_}j$, a composited volume data set out of $P_{Og\_}(j+1)$ through $P_{Og\_}(j+60)$ where the overlapping region with $P_{Og\_}j$ is 50% or more.

<S250: Process of Estimating Amount of Positional Displacement of Composited Volume Data Sets>

Next, the amount of positional displacement of each composited volume data set due to change in the relative positional relationship between the object and the reception unit of photoacoustic waves in time intervals between irradiations by light is estimated. In the present embodiment, the position estimation unit 560 acquires the amount of positional displacement among composited volume data sets as information relating to positional displacement among composited volume data sets. An example of an image processing method of estimating the amount of positional displacement of the composited volume data sets will be described below with reference to FIG. 7, which is a detailed processing flow of S250.

<S251: Process of Acquiring Similarity Function Among Composited Volume Data Sets>

The position estimation unit 560 acquires a similarity function F_k between $P_{Og\_}k1$ and $P_{Og\_}k2$, as shown in Expression (1).

$$F\_k(x,y,z)=f_{simil}(P_{Og\_}k,x,y,z) \qquad \text{Expression (1)}$$

Thus similarity function F_k is a function for calculating the similarity of translating the relative position (x, y, z) of the composited volume data $P_{Og\_}k2$ that is one of the pair R_k as to the other composited volume data $P_{Og\_}k1$. Note that the function $f_{simil}$ here returns a high value as a function value in a case where the similarity between the images is high. Acquisition of the similarity function F_k means acquiring a function value in a case of discretely changing the amount of translation (x, y, z) that is the argument of the functions, i.e., changing the relative position among the images, within a predetermined range. For example, in a case of changing the values of each of x, y, and z, as integer values within the range of −L to +L, this means acquiring a group of (2L+1)×(2L+1)×(2L+1) values that F_k returns for each. As a further advancement, the group of (2L+1)×(2L+1)×(2L+1) values may be subjected to bilinear or bicubic interpolation or the like, to derive a similarity function F_k that is information closer to a continuous function, and obtained.

Note that a position that has been translated by an amount equivalent to the relative position of $P_{Og\_}k2$ as to $P_{Og\_}k1$ (the amount of movement of the reception unit 200 at time intervals between irradiation by light) may be used as a standard, and a function value obtained in a case where the position of $P_{Og\_}k2$ is discretely moved within a predetermined range.

Any measure of similarity can be used for the function to calculate similarity, such as sum of squared difference (SSD), sum of absolute difference (SAD), mutual information, mutual correlation, or the like, for example. Alternatively, forms having features may be extracted from the composited volume data, and similarity functions may be obtained by measuring the degree of matching the positions thereof. Features to be extracted may be features extracted in known technology that are generally used in the field of image processing, such as anatomical features like blood vessels or the like, edge detection, corner detection, or the like. Features to be extracted may also be high-order local image features or the like, such as scale-invariant feature transform (SIFT) features or Speeded Up Robust Features (SURF) generally used in the technical field of computer vision or the like. It is conceivable that these methods can allow more robust similarity functions to be obtained with regard to difference in luminance distribution among the composited volume data sets, inclusion of noise, and the like.

The position estimation unit 560 may acquire a similarity function by subjecting the results of similarity calculation (calculation of squaring differences of each pixel value in the case of SSD) at each position shown in Expression (1) by the weight volume data Wg_j described in S240. According to this processing, the position estimation unit 560 can acquire a similarity function that strongly reflects regions in the composited volume data where reliability is high.

In a case where the similarity among composited volume data sets that are the object of similarity calculation cannot be calculated correctly, the results thereof do not have to be used in subsequent processing. Conceivable examples of cases where similarity cannot be calculated correctly include cases where similarity is small regardless of whatever translation, the similarity does not change, and so forth. According to this processing, comparison results (similarity functions) among composited volume data sets where the same features are sufficiently manifested can be selectively used in subsequent processing.

<S252: Process of Acquiring Translation Amount where Similarity Function is Largest>

Next, the position estimation unit 560 acquires translation amount M_k(x, y, z) of the composited volume data $P_{Og\_}k2$ as to the composited volume data $P_{Og\_}k1$ where the function value of similarity function F_k is largest, as shown in Expression (2).

$$M\_k(x,y,z) = \operatorname{argmax}\{(F\_k(x,y,z)\} \quad \text{Expression (2)}$$

The position estimation unit 560 acquires the translation amount M_k where the function value of the similarity function F_k is largest for each pair.

<S253: Process of Acquiring Reliability of Similarity Function Based on Similarity Function>

Next, the position estimation unit 560 acquires a reliability S_k of the similarity function F_k, based on the similarity function F_k. The reliability of a similarity function is a parameter representing the likelihood of the translation amount (relative position between images) where the similarity function is the largest, that is obtained based on the similarity function. In other words, the reliability of the similarity function is a parameter representing the likelihood of the positional relationship between composited volume data sets to be compared, that is acquired based on the similarity function. For example, the acutance of the similarity function may be used as the reliability of the similarity function. That is to say, a value based on the magnitude in change (acutance) of similarity functions values around a position where the similarity function is greatest may be taken as the similarity. Specifically, the position estimation unit 560 acquires the similarity S_k representing the acutance from Expression (3) according to a secondary differential value of the similarity function F_k.

[Math. 1]

$$S\_k = (S\_k(x) \ S\_k(y) \ S\_k(z))^T \quad \text{Expression (3)}$$
$$= \left( \frac{\partial^2 F\_k(x, y, z)}{\partial^2 x}, \frac{\partial^2 F\_k(x, y, z)}{\partial^2 y}, \frac{\partial^2 F\_k(x, y, z)}{\partial^2 z} \right)$$

Note that any method may be used by the position estimation unit 560, as long as a parameter can be acquired that represents the likelihood of the translation amount (relative position between images) where the similarity function is the largest, based on the similarity function.

<S254: Process of Acquiring Position Information of Composited Volume Data after Positional Displacement, Based on Reliability of Similarity Function>

In a case of estimating the position of composited volume data, an evaluation function is defined where the translation amount M_k that is an individual optimal value of the pair R_k is maximally maintained. That is to say, an evaluation function is defined where the value becomes lower as the position of $P_{Og\_}k2$ as to $P_{Og\_}k1$ is farther away from the translation amount M_k. Further, this evaluation value thus defined is weighted using the reliability S_k of the similarity function acquired in S253. Expression (4) represents an example of an evaluation value E_k weighted by the S_k of the similarity function.

$$E\_k = S\_k \times (M\_k - (PosP_{Og\_}k1 - PosP_{Og\_}k2))^2 = S\_k(x) \times$$
$$(M\_k(x) - (PosP_{Og\_}k1(x) - PosP_{Og\_}k2(x)))^2 + S\_k(y) \times$$
$$(M\_k(y) - (PosP_{Og\_}k1(y) - PosP_{Og\_}k2(y)))^2 + S\_k(z) \times$$
$$(M\_k(z) - (PosP_{Og\_}k1(z) - PosP_{Og\_}k2(z)))^2 \quad \text{Expression (4)}$$

$PosP_{Og\_}k1$ represents the position of $P_{Og\_}k1$ as to the reference position. $PosP_{Og\_}k2$ represents the position of $P_{Og\_}k2$ as to the reference position. Note that at the time of defining the evaluation function, the similarity function F_k may approximate a quadratic function that fits this similarity function F_k. In a case the similarity function F_k can be approximated by decreasing following the quadratic function in the vicinity of the translation amount M_k, Expression (3) is a function that approximates the value of the similarity function F_k in the vicinity of the translation amount M_k from the positional relationship between $P_{Og\_}k1$ and $P_{Og\_}k2$.

Next, the position estimation unit 560 acquires all composited volume data positions $PosP'_{Og\_}j$ as to the reference position for when a cost function E defined as in Expression (5) is minimized.

[Math. 2]

$$E = \sum_{k=1}^{K} \mathrm{E\_k} \quad \text{Expression (5)}$$

$$= \sum_{k=1}^{K} S\_k \bullet (M\_k - (PosP_{0g}\_k1 - PosP_{0g}\_k2))^2$$

$$\sum_{k=1}^{K} \begin{bmatrix} S\_k \times (M\_k - (PosP_{0g}\_k1(x) - \\ (PosP)_{0g}\_k2(x)))^2 + S\_k(y) \times (M\_k(y) - \\ (PosP_{0g}\_k1(y) - PosP_{0g}\_k2(y)))^2 + \\ S\_k(z) \times (M\_k(z) - \\ (PosP_{0g}\_k1(z) - PosP_{0g}\_k2(z)))^2 \end{bmatrix}$$

The position of the composited volume data as to the reference position when the cost function is minimized represents the position information of the composited volume data after the positional displacement due to change in the relative positional relationship between the object 900 and reception unit 200.

Using an evacuation function weighted by the reliability of the similarity function enables position information that strongly reflects the evaluation result of the pair of image data containing common structure to be acquired. On the other hand, position information can be acquired without strongly reflecting evaluation of a pair of image data not containing common structure in the image data. That is to say, position information of volume data can be acquired with precision by using the reliability of the similarity function.

For example, the position estimation unit 560 performs solving by the linear least-squares method for a solution where the cost function E shown in Expression (5) is minimized (most closely approaches zero). Accordingly, the composited volume data position PosP'$_{0g}$_j of each composited volume data set can be uniquely calculated. Since the composited volume data position PosP'$_{0g}$_j of each composited volume data set can be uniquely calculated by the linear least-squares method in the cost function shown in Expression (5), the calculation cost is small.

The cost function optimization by linear optimization described above is not restrictive; any known method may be used for cost function optimization. For example, optimization may be performed using non-linear optimization methods by iterative calculation, such as the steepest descent method. Newton's method, or the like. That is to say, the position estimation unit 560 acquires position information of composited volume data as to the reference position after positional displacement, by searching for a position for each composited volume data where the cost function is minimized.

Note that the cost function may be defined so as to normalize the expected change (movement) of each composited volume data position at intervals between irradiation by light. In a case where the object is a breast, movement due to breathing will be expected to be dominant. In this case, the movement of the object is expected to be around several millimeters at the most, and the movement thereof to be continuous and smooth. The movement is also expected to be cyclic. Normalization can be performed so as to suppress calculation of movement that is far removed from the expected movement of the object such as described above.

Any method may be used for normalization. For example, normalization can be performed by calculating the cost function by multiplying the summation of the amount of movement (distance of moment) of the object over the process of derivation by a predetermined weighting coefficient. Alternatively, the summation of temporal differentiation (acceleration) of the change of the object may be added into the cost function. Further, a value calculated based on a frequency component value of the change of the object may be added into the cost function. Moreover, a model of typical change of the object may be prepared, with the different as to the change in the model added into the cost function as cost.

Further, "minimizing the cost function" is not restricted to cases where the cost function is strictly at the minimum, and also includes cases where the value of the cost function is equal to or below a predetermined value when solution candidates are changed, and cases where the amount of change of the cost function is equal to or below a predetermined value. That is to say, the position estimation unit 560 may determine that the cost function has been minimized by the cost function satisfying predetermined conditions. Further, the user may use the input unit 700 to instruct that the cost function has been minimized. In this case, the position estimation unit 560 determines that the cost function has been minimized upon receiving the instruction form the input unit 700.

<S255: Process of Acquiring Positional Displacement of Composited Volume Data Based on Position Information after Positional Displacement>

Next, the position estimation unit 560 acquires positional displacement amount M$_g$_j of the composited volume data where the cost function has been minimized, with regard to the composited volume data acquired in S230. This positional displacement amount M$_g$_j represents the positional displacement at each composited volume data set due to relative positional relation change between the object 900 and the reception unit 200.

FIG. 8 illustrates position PosP$_{0g}$_2 of composited volume data P$_{0g}$_2 acquired in S230, and position PosP'$_{0g}$_2 of composited volume data P'$_{0g}$_2 where the cost function has been minimized (position after positional displacement). FIG. 8 illustrates the composited volume data P$_{0g}$_2 by solid lines and the composited volume data P'$_{0g}$_2 where the cost function has been minimized by dashed lines.

The position information after positional displacement of the composited volume data can be precisely estimated based on the reliability of the similarity function in S254, so the positional displacement amount of the composited volume data is also precisely acquired in S255.

Note that any technique may be used in S250, as long as the positional displacement amounts of the composited volume data sets due to change in relative position between the object 900 and reception unit 200 can be acquired based on the reliability of the similarity function. Using composited volume data where quality has been improved as compared to pulse volume data is used in S250, so the amount of positional displacement of the composited volume data can be estimated with precision.

<S260: Process of Estimating Positional Displacement Amount of Pulse Volume Data>

The position estimation unit 560 estimates the positional displacement M$_p$_i of the pulse volume data based on the positional displacement amount Mg_j of the composited volume data estimated in S250. That is to say, the position estimation unit 560 estimates the positional displacement as to the position of the pulse volume data set in S210.

The position estimation unit 560 can allocate the positional displacement amount of the composited volume data estimated in S250 for the positional displacement amount of pulse volume data correlated with the composited volume data. Positional displacement amount of other pulse volume data an be estimated by the position estimation unit 560 performing interpolation processing as to the positional displacement amount of the pulse volume data that has been allocated. Known techniques such as linear interpolation and spline interpolation and the like can be employed for the interpolation technique. Interpolation processing may also be performed with constraints so that there is no calculation of movement that is far removed from the expected movement of the object described in S250.

Any pulse volume data set out of the pulse volume data sets that are the object of compositing may be taken as a pulse volume data set correlated with the composited volume data. For example, in a case where the number of the pulse volume data sets to be composited is an odd number, the pulse volume data set at the temporal center may be correlated with the composited volume data.

Also, in a case where the number of the pulse volume data sets to be composited is an even number, any pulse volume data set around the temporal center may be correlated with the composited volume data. For example, in a case where ten pulse volume data sets are the object of compositing as in the present embodiment, the positional displacement amount $M_{g\_}j$ of the composited volume data $P_{Og\_}j$ may be allocated as the positional displacement amount $M_{p\_}5i$ of the pulse volume data $P_{Op\_}5j$.

Also, in a case where the number of the pulse volume data sets to be composited is an even number, a virtual pulse volume data set situated at the temporal center may be correlated with the composited volume data. For example, in a case where ten pulse volume data sets are the object of compositing as in the present embodiment, the positional displacement amount of the composited volume data $P_{Og\_}j$ may be allocated as the positional displacement amount of a virtual pulse volume data set where the pulse index is 5.5j.

Also, in a case of compositing with weighting, the pulse volume data set that has been weighted with the highest weighting coefficient out of all pulse volume data sets that are the object of compositing may be correlated with the composited volume data. Alternatively, the pulse volume data of which the weighting coefficient is a median value of all pulse volume data sets that are the object of compositing may be correlated with the composited volume data.

FIG. 9 illustrates an example of processing of estimating the positional displacement amount of pulse volume data in the present embodiment. FIG. 9A is a diagram indicating the positional displacement amount as to pulse volume data before performing later-described positional displacement correction with an arrow. First, the position estimation unit 560 allocates the positional displacement amount $M_{g\_}2$ of the composited volume data $P_{Og\_}2$ to the positional displacement amount $M_{g\_}10$ of the pulse volume data $P_{Og\_}10$ that is indicated by hatching, as illustrated in FIG. 9A. The position estimation unit 560 also allocates the positional displacement amount $M_{g\_}j$ of the other composited volume data $P_{Og\_}j$ to the pulse volume data $P_{Og\_}5j$. $M_{g\_}1$ is 0 in the present embodiment, so $M_{g\_}5$ also is 0. Note that FIG. 9A illustrates the position PosP'$_{Og\_}10$ of the pulse volume data after positional displacement.

Next, as illustrated in FIG. 9B, the position estimation unit 560 acquires translation amount other than the pulse volume data $P_{Og\_}5j$ indicated by hatching, by linear interpolation of positional displacement amount $M_{p\_}5j$. FIG. 9B illustrates the positional displacement amount $M_{p\_}5j$ by solid lines, and positional displacement amounts other than the positional displacement amount $M_{p\_}5j$ that have been estimated by interpolation by dotted lines. Interpolating the positional displacement amount so as to connect the positions PosP'$_{Og\_}i$ of the pulse volume data after positional displacement enables the positional displacement amount of each pulse volume data set to be estimated. Note that a position obtained by interpolating the position PosP'$_{Op\_}j$ of the composited volume data P'$_{Og\_}j$ after optimization may be estimated to be the position of the pulse volume data after positional displacement. Also, the positional displacement amount of the pulse volume data may be accrued based on the position of pulse volume data after positional displacement that has been obtained in this way. According to the above-described processing, the positional displacement amount of each pulse volume data set can be acquired based on the positional displacement amount of each composited volume data set.

In this process, positional displacement amount of pulse volume data can be estimated based on the positional displacement amount of composited volume data that has been estimated with high precision. Accordingly, the estimation precision of the positional displacement amount of pulse volume data is higher as compared to a case of directly estimating the positional displacement amount from low-quality pulse volume data.

Also, the number (M) of composited volume data is smaller than the number (N) of pulse volume data in the present embodiment, as mentioned earlier. In this case, the technique of estimating the positional displacement of all composited volume data by comparing composited volume data sets with each other requires less calculation amount as compared to a technique of estimating the positional displacement of all pulse volume data by comparing pulse volume data sets with each other. Accordingly, the technique where the positional displacement amount of all pulse volume data is estimated based on the positional displacement amount of all composited volume data obtained by the latter, has a lower calculation cost as compared to the former technique of estimating positional displacement of all pulse volume data.

<S270: Process of Compositing Multiple Pulse Volume Data Sets after Positional Displacement Correction>

After having performed processing to correct the position of each pulse volume data set by the positional displacement amount estimated in S260 (translation processing), the compositing unit 540 composites these so as to acquire third composited volume data (third composited image data). That is to say, the compositing unit 540 composites the pulse volume data sets situated at positions after positional displacement to acquire the third composited volume data. The compositing for acquiring the third will be referred to as third compositing.

FIGS. 10A through 10E illustrate an example of positional displacement correction processing (translation processing) in this process. FIG. 10A illustrates part of the pulse volume data sets ($P_{Op\_}23$ through $P_{Op\_}25$) before the translation processing according to the present embodiment. The dashed line represents a feature 701 at the perimeter of the $P_{Op\_}25$ and within the $P_{Op\_}25$. The solid line represents a feature 711 at the perimeter of and within the $P_{p\_}24$. The dotted line represents a feature 721 at the perimeter of and within the $P_{p\_}23$. Note that the feature 701, feature 711, and feature 721 all represent the same feature. In the state in FIG. 10A, the feature within each pulse volume data set is situated at different positions.

FIG. 10B illustrates pulse volume data P'$_{Op\_}25$ after having translated the pulse volume data set $P_{Og\_}25$ before translation, by the positional displacement amount $M_{p\_}25$ estimated in S260. FIG. 10C illustrates pulse volume data $P'_{Op\_}24$ after having translated the pulse volume data set $P_{Op\_}24$ before translation, by the positional displacement amount $M_{p\_}24$ estimated in S260. FIG. 10D illustrates pulse volume data $P'_{Op\_}23$ after having translated the pulse volume data set $P_{Op\_}23$ before translation, by the positional displacement amount $M_{p\_}23$ estimated in S260.

FIG. 10E illustrates the pulse volume data $P'_{Op\_}23$, $P'_{Op\_}24$, and $P'_{Op\_}25$ overlaid after translation. The features 701, 711, and 721 within each pulse volume data set are overlaid at approximately the same position in FIG. 10E. The compositing unit 540 composites the pulse volume data sets that have been subjected to translation processing as illustrated in FIG. 10E, and thus can acquire positioned volume data. The positioned volume data is equivalent to the third composited volume data. Note that "positioning" means top perform both of positional displacement correction processing (translation processing) and compositing processing.

The compositing technique described in S240, a compositing technique where only optional pulse volume data is retained, or the like, can be applied in this process to regions where pulse volume data sets are superimposed.

The pulse volume data sets can be subjected to positional displacement correction based on precisely estimated positional displacement amounts using composited volume data, and thereafter composited. Thus, image data can be acquired where the effects of change in relative positional relationship between the object and the reception unit of photoacoustic waves at time intervals between irradiations by light, that are included in composited volume data, have been suppressed (positioned volume data).

The above-described processing can be applied even in a case where the reception unit 200 does not move between irradiations by light. That is to say, the above-described processing can be applied even in a case where the photoacoustic apparatus does not have a driving unit 300. In this case as well, image data can be acquired where the effects of change in relative positional relationship between the object and the reception unit of photoacoustic waves at time intervals between multiple irradiations by light have been suppressed.

(Example of Positional Displacement Correction Taking into Consideration Rotation or Deformation)

Description has been made in the present embodiment regarding an example of a case where translation occurs as change in the relative positional relationship between the object and reception unit. Note however, that the present invention can be applied to case where rotation and deformation occur as this change. That is to say, the apparatus according to the present embodiment may acquire information relating to positional displacement due to at least one of translation, rotation, and deformation, as information relating to positional displacement.

For example, in a case of taking rotation into consideration, the position estimation unit 560 can estimate the positions and rotation amounts (positional displacement amounts) of each composited volume data set, using the rotation amount as an argument in addition to the translation amount in S250. Next, the position estimation unit 560 can estimate the positions and rotation amounts (positional displacement amounts) of each pulse volume data set, based on the positions and rotation amounts (positional displacement amounts) of each composited volume data set. Next, the position estimation unit 560 can acquire the third composited volume data by performing the third compositing after having subjecting each pulse volume data sets to rigid body transform (positional displacement correction processing) based on the estimated position and amount of rotation in S270. An arrangement may be made where just the amount of rotation is the positional displacement amount.

Again, for example, in a case of taking deformation into consideration, the position estimation unit 560 can estimate the displacement, using the displacement amount (at least one of translation and rotation amount) at each point set in composited volume data as an argument in S250. Next, the position estimation unit 560 can estimate the displacement amount at each point of each pulse volume data sets set, based on the displacement amount at each point of each composited volume data set in S260. Next, in S270 the position estimation unit 560 performs deformation processing (positional displacement correction processing) of each pulse volume data sets based on the estimated displacement, and thereafter performs the third compositing, and thus can acquire the third composited volume data. The displacement amount among composited volume data sets can be calculated by techniques that express deformation, such as free-form deformation (hereinafter referred to as "FFD") and thin plate splines, for example. High-order change including deformation can be taken into consideration by such processing, and thus high-quality third composited volume data can be acquired.

(Example of Holding Object)

The photoacoustic apparatus may have an object holding portion 1000 that holds the object 900 as illustrated in FIG. 11. A breast of a living body 1200 lying in a prone position on a bed 1100 is the object 900 in FIG. 11. The object holding portion 1000 is a member for suppressing movement of the object 900. Examples of material that can be used for the object holding portion 1000 include polymethylpentene, polyethylene terephthalate, and so forth. In a case of irradiating the object 900 by light 130 via the object holding portion 1000 as illustrated in FIG. 11, the object holding portion 1000 may be transparent to the light 130. The object holding portion 1000 may be configured such that the holding face of the object holding portion 1000 and the outer shape of the object 900 generally match.

In a case where movement of the object 900 is restricted to a particular direction by the object holding portion 1000 for example, the position estimation unit 560 may perform positional displacement correction in the particular direction alone. That is to say, the position estimation unit 560 may acquire position information after the positional displacement, without taking into consideration positional displacement other than in the direction to which the positional displacement is suppressed by the object holding portion 1000. This can reduce the amount of processing necessary for the positional displacement correction.

Although an example of imaging a breast in a state where the living body 1200 is lying in a prone position has been described in FIG. 11, the photoacoustic apparatus according to the present embodiment is not restricted to the prone position, and the object 900 can be imaged in any position.

(Example of Displaying Pulse Volume Data)

Although an example of starting acquisition of pulse volume data after measurement of photoacoustic waves by full-light irradiation is complete has been described in the present embodiment, pulse volume data may be acquired sequentially at each irradiation by light. In the case of the latter, the acquired pulse volume data may be sequentially display on the display unit 600. Accordingly, the pulse volume data that has already been acquired can be confirmed by the user before all measurement is completed. Regions where the pulse volume data sets are superimposed may be composited by the compositing technique described in S270.

(Example of Position Estimation Based on MIP Image)

After the three-dimensional image data is converted into two-dimensional projection data, the positions of each of the composited volume data sets after positional displacement as to the reference position may be estimated in S250. The following is a description of this.

The projection data acquisition unit 550 acquires MIP data as projected data projected in each of the X direction, Y direction, and Z direction, for the composited initial sound pressure distribution data $P_{0g\_}j(x, y, z)$. The MIP data projected in the X direction is two-dimensional spatial distribution information represented by the Y axis and Z axis, and is expressed as $I_{xg\_}j(y, z)$. The MIP data projected in the Y direction is two-dimensional spatial distribution information represented by the Z axis and X axis, and is expressed as $I_{yg\_}j(z, x)$. The MIP data projected in the Z direction is two-dimensional spatial distribution information represented by the X axis and Y axis, and is expressed as $I_{zg\_}j(x, y)$. The values at each position of each MIP data set are expressed by function expressions such as $I_{xg\_}j(y, z)$, $I_{yg\_}j(z, x)$, and $I_{zg\_}j(x, y)$.

Note that projection techniques other than MIP images can be employed, as long as three-dimensional image data can be converted into two-dimensional data. For example, minimum intensity projection (MinP) image may be generated and used instead of MIP images. Further, multiple slides in the projection direction may be added in to acquire projection data.

Next, the position estimation unit 560 acquires the similarity between the MIP data of $P_{0g\_}k1$ and the MIP data of $P_{0g\_}k2$ for each of the X-Y plane, Y-Z plane, and Z-X plane. That is to say, the position estimation unit 560 acquires the similarity as shown in Expressions (6) through (8).

$$FX\_k(y,z) = f_{simil}(I_{xg\_}k,y,z) \quad \text{Expression (6)}$$

$$FY\_k(x,z) = f_{simil}(I_{yg\_}k,x,z) \quad \text{Expression (7)}$$

$$FZ\_k(x,y) = f_{simil}(I_{zg\_}k,x,y) \quad \text{Expression (8)}$$

Here, FX_k(y, z) is a function to calculate the similarity in a case of translating the relative position of one MIP data set making up the pair R_k by (y, z) as to the other MIP data set, with regard to the MIP data expressed by the Y-Z plane. FY_k(x, z) is a function relating to the Z-X plane, and FZ_k(x, y) is a function relating to the X-Y plane. Note that technique described in S250 may be used for the similarity calculation technique.

Next, translation amounts MX_k, MY_k, and MZ_k, of $P_{0g\_}k$ as to $P_{0g\_}k1$ where the function value is the largest, are calculated for each of the Y-Z plane, Z-X plane, and X-Y plane, as shown in Expressions (9) through (11).

[Math. 3]

$$MX\_k = (MX\_k(y), MX\_k(z)) = \underset{y,z}{\operatorname{argmax}}\{FX\_k(y, z)\} \quad \text{Expression (9)}$$

[Math. 4]

$$MY\_k = (MY\_k(x), MY\_k(z)) = \underset{x,z}{\operatorname{argmax}}\{FY\_k(x, z)\} \quad \text{Expression (10)}$$

[Math. 5]

$$MZ\_k = (MZ\_k(x), MZ\_k(y)) = \underset{x,y}{\operatorname{argmax}}\{FZ\_k(y, z)\} \quad \text{Expression (11)}$$

For example, the average values of the components of the coordinate axes for translation amounts MX_k, MY_k, and MZ_k, are the component values of three-dimensional translation amount M_k of $P_{0g\_}k$ as to $P_{0g\_}k1$, where the similarity is the greatest, as shown in Expression (12) for example.

[Math. 6]

$$M\_k = (M\_k(x), M\_k(y), M\_k(z)) \quad \text{Expression (12)}$$
$$= \left(\frac{MY\_k(x) + MZ\_k(x)}{2}, \frac{MX\_k(y) + MZ\_k(y)}{2}, \frac{MX\_k(z) + MY\_k(z)}{2}\right)$$

The position estimation unit 560 also calculates the secondary differentiation value of the similarity function F_k for each coordinate axis, thereby acquiring S_k(x), S_k(y), and S_k(z), which are the reliability of the similarity functions, as shown in Expressions (13) through (15).

[Math. 7]

$$S\_k(x) = \frac{\partial^2 FY\_k(x, z)}{\partial^2 x} + \frac{\partial^2 FZ\_k(x, y)}{\partial^2 x} \quad \text{Expression (13)}$$

[Math. 8]

$$S\_k(y) = \frac{\partial^2 FY\_k(y, z)}{\partial^2 y} + \frac{\partial^2 FZ\_k(x, y)}{\partial^2 y} \quad \text{Expression (14)}$$

[Math. 9]

$$S\_k(y) = \frac{\partial^2 FY\_k(x, z)}{\partial^2 z} + \frac{\partial^2 FZ\_k(x, y)}{\partial^2 z} \quad \text{Expression (15)}$$

Next, the position estimation unit 560 can use the translation amount M_k shown in Expression (12) and the reliability of the similarity functions shown in Expressions (13) through (15) to estimate the positions of the composited volume data when the cost function shown in Expression (5) is minimized, as described in S250.

According to the above-described processing, the positions of the composited volume data sets as to the reference position can be acquired based on the two-dimensional data converted form the there-dimensional data. Converting three-dimensional into two-dimensional allows the position of composited volume data after positional displacement to be acquired with a calculation cost smaller in comparison with a case of performing the processing to the three-dimensional without conversion.

(Example of Positional Displacement Correction of Reception Position Information)

The photoacoustic apparatus according to the present embodiment may correct position information of the receptors used to acquire initial sound pressure distribution data, at each time of irradiation by light, based on the positional displacement amount corresponding to each irradiation by light. That is to say, the photoacoustic apparatus according to the present embodiment may correct reception position information of photoacoustic waves at each time of irradiation by light. The processing of correcting the positional displacement of reception position information will be described in detail with reference to the processing flowchart illustrated in FIG. 12. Note that process the same as those in FIG. 3 are denoted by the same symbols, and description will be omitted.

<S280: Process of Correcting Position Information of Receptor>

First, the reconstruction unit 520 acquires position information of each receptor not taking into consideration positional displacement. For example, the reconstruction unit 520 can acquire position information of each receptor without taking positional displacement into consideration, by reading out position information of the receptors at the time of irradiation by light, that has been stored in the storage unit 510 beforehand. Alternatively, the reconstruction unit 520 may acquire position information of each receptor without taking positional displacement into consideration, by accepting position information of the reception unit 200 from a position sensor provided to the driving unit 300 with irradiation by light as a trigger.

Next, the reconstruction unit 520 corrects the positions corresponding to position information, of the receptors without taking positional displacement at the time of irradiation into consideration (translation processing). Accordingly, the reconstruction unit 520 can acquire position information of the receptors that have been subjected to positional displacement correction at each irradiation by light. That is to say, the reconstruction unit 520 acquires position information after positional displacement of the receptors (information relating to position) based on the positional displacement amount of the pulse volume data acquired in S260.

<S290: Process of Acquiring Volume Data Based on Position Information of Receptors after Positional Displacement>

The reconstruction unit 520 acquires image data in the form of volume data, based on multiple electrical signal groups stored in the storage unit 510, and position information of the receptors after positional displacement that has been obtained in S280. In this process, the reconstruction unit 520 may reconstruct a region smaller than the entire imaging region from an electrical signal group corresponding to a single irradiation by light, and repeat this for all irradiations by light, thereby generating one volume data set, as described in S210. The reconstruction unit 520 may also generate one volume data set by reconstructing the entire imaging region from electrical signal groups corresponding to each irradiation by light. In this case, in this process the reconstruction unit 520 acquires multiple pulse volume data sets corresponding to the multiple irradiations by light, and the compositing unit 540 composites the multiple image data sets. In the present embodiment, the multiple pulse volume data sets obtained in S210 are equivalent to a first plurality of image data sets, and the multiple pulse volume data sets obtained in S290 are equivalent to a second plurality of image data sets.

Note that an arrangement may be made in the present embodiment where pulse volume data is not generated in S210, and a desired combination of electrical signal groups is selected in S220, with the composited volume data being generated in S230 using the selected electrical signal groups. In this case, the electrical signal groups may be selected using the same method as selecting the pulse volume data sets described in S220.

(Example of Acquiring Position Information after Positional Displacement, Based on Reliability of Similarity Function of Pulse Volume Data)

The photoacoustic apparatus according to the present embodiment may acquire position information of the pulse volume data sets after positional displacement, based on the reliability of the similarity function of the pair of pulse volume data sets. That is to say, the image processing method of acquiring position information using the reliability information of the pulse volume data sets may be applied to pulse volume data. Note that the image data to be subjected to the image processing of the present embodiment may be any image data, as long as a similarity function between image data sets can be acquired.

Examples Other than Photoacoustic Apparatus

Although an embodiment of the present invention has been described by way of an example using a photoacoustic apparatus, the scope of application of the present invention is not restricted to this. Rather, the present invention is applicable to all apparatus that acquire position information of multiple image data sets. For example, the position information acquisition method according to the present invention may be applied to multiple ultrasound image data sets acquired by an ultrasound diagnosis apparatus that acquires image data by transmitting and receiving ultrasound. Further, the present invention is not restricted to image data obtained using acoustic waves, and the position information acquisition method according to the present invention may be applied to multiple image data sets acquired using light, in diffuse optical tomography (DOT) apparatuses or optical coherence tomography (OCT) apparatuses for example. Further, the position information acquisition method according to the present invention may be applied to multiple image data sets acquired using X-rays in a radioscopic image acquisition apparatus or tomographic image acquisition apparatus or the like.

Other Embodiments

The present invention may also be realized executing the following processing. That is to say, software (program) realizing the functions of the above-described embodiment is supplied to a system or apparatus via network or various types of recording media, and the system or computer of the apparatus (or CPU, microprocessor unit (MPU), etc.) reads out and executes the program.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-138112, filed Jul. 9, 2015 and Japanese Patent Application No. 2015-138113, filed Jul. 9, 2015, which are hereby incorporated by reference herein in their entirety.

The invention claimed is:

1. An apparatus comprising:
a first acquisition unit configured to acquire a first plurality of image data sets;
a second acquisition unit configured to acquire first composited image data using a first two or more image data sets of the first plurality of image data sets;
a third acquisition unit configured to acquire second composited image data, using a second two or more image data sets of the first plurality of image data sets, the second two or more image data sets being a combination different from the first two or more image data sets;
a fourth acquisition unit configured to acquire information relating to positional displacement between the first composited image data and the second composited image data, using the first composited image data and the second composited image data; and
a fifth acquisition unit configured to acquire information relating to positional displacement of the first plurality of image data sets, using information relating to the positional displacement between the first composited image data and the second composited image data.

2. The apparatus according to claim 1, further comprising:
a sixth acquisition unit configured to acquire third composited image data, by positioning the first plurality of image data sets using information relating to the positional displacement of the first plurality of image data sets.

3. The apparatus according to claim 1, further comprising:
a reception unit configured to receive acoustic waves generated from an object by being irradiated by light a plurality of times; and
a signal acquisition unit configured to acquire a plurality of signals corresponding to the plurality of times of irradiation by light, output by the receiving unit having received the acoustic waves;
wherein the first acquisition unit acquires the first plurality of image data sets using the plurality of signals.

4. The apparatus according to claim 3,
wherein the second acquisition unit selects, from the first plurality of image data sets, the first two or more image data sets corresponding to two or more irradiations by light performed during a first period,
and wherein the third acquisition unit selects, from the first plurality of image data sets, the second two or more image data sets corresponding to two or more irradiations by light performed during a second period that is different form the first period.

5. The apparatus according to claim 4,
wherein the second acquisition unit selects, from the plurality of image data sets, the first two or more image data sets corresponding to two or more irradiations by light performed temporally consecutively within the first period,
and wherein the third acquisition unit selects, from the plurality of image data sets, the second two or more image data sets corresponding to two or more irradiations by light performed temporally consecutively within the second period.

6. The apparatus according to claim 4, further comprising:
a sixth acquisition unit configured to acquire third composited image data, by positioning the first plurality of image data sets using information relating to the positional displacement of the first plurality of image data sets,
wherein the second acquisition unit
acquires information relating to image quality of the third composited image data, using the third composited image data, and
selects the first two or more image data sets from the plurality of image data sets, using information relating to image quality of the third composited image data.

7. The apparatus according to claim 3, further comprising:
a seventh acquisition unit configured to acquire information relating to the position of the reception unit during the plurality of times of irradiation by light, using information relating to positional displacement of the first plurality of image data sets, and acquire image data using the information relating to position and the plurality of signals.

8. The apparatus according to claim 7,
wherein the seventh acquisition unit
acquires a second plurality of image data sets corresponding to the plurality of times of irradiation by light, using the information relating to position and the plurality of signals, and
acquires the image data by positioning the second plurality of image data sets.

9. The apparatus according to claim 1,
wherein the fifth acquisition unit performs interpolation processing regarding information relating to positional displacement between the first composited image data and the second composited image data, to acquire information relating to positional displacement of the plurality of image data sets.

10. The apparatus according to claim 1,
wherein the second acquisition unit and the third acquisition unit select the first two or more image data sets and the second two or more image data sets such that the first composited image data and the second composited image data overlap.

11. The apparatus according to claim 1,
wherein the fourth acquisition unit
acquires a reliability of a similarity function representing a relationship between a relative position between the first composited image data and the second composited image data, and a similarity between the first composited image data and the second composited image data, and
acquires information relating to positional displacement between the first composited image data and the second composited image data, using the reliability of the similarity function.

12. The apparatus according to claim 11,
wherein the fourth acquisition unit acquires an acutance of the similarity function at the relative position where the similarity is largest, as the reliability of the similarity function.

13. The apparatus according to claim 11,
wherein the fourth acquisition unit acquires a secondary differentiation of the similarity function at the relative position where the similarity is largest, as the reliability of the similarity function.

14. The apparatus according to claim 11,
wherein the fourth acquisition unit acquires information relating to position of the plurality of image data sets where a cost function is smallest, the cost function defined by weighting by the reliability of the similarity an evaluation function based on difference between the relative position as an argument and the relative position where the similarity is the greatest.

15. The apparatus according to claim 1, further comprising:
a light irradiation unit; and
a reception unit configured to output signals by receiving acoustic waves generated from an object that has been irradiated by light from the light irradiation unit,
wherein the light irradiation unit irradiates the object with light a plurality of times,
wherein the reception unit outputs a plurality of signals corresponding to the plurality of irradiations by light, by receiving photoacoustic waves generated from the object from the plurality of times of irradiation by light,
wherein the first acquisition unit acquires a plurality of image data sets of the object corresponding to the plurality of times of irradiation by light, based on the plurality of signals,
wherein the second acquisition unit selects, from the plurality of image data sets, the first two or more image data sets corresponding to the two or more irradiations by light performed during the first period,
and wherein the third acquisition unit selects, from the plurality of image data sets, the second two or more image data sets corresponding to the two or more irradiations by light performed during the second period that is different from the first period.

16. The apparatus according to claim 15, further comprising:
a driving unit configured to move the reception unit during a period where the plurality of irradiations by light are performed.

17. The apparatus according to claim 16,
wherein the first acquisition unit acquires the first plurality of image data sets, by acquiring image data in a region larger than the amount of movement of the reception unit during an interval of time of irradiation by light, using signals corresponding to irradiation by light for one time.

18. A method comprising:
acquiring a first plurality of image data sets;
acquiring first composited image data using a first two or more image data sets of the first plurality of image data sets;
acquiring second composited image data, using a second two or more image data sets of the first plurality of image data sets, the second two or more image data sets being a combination different from the first two or more image data sets;
acquiring information relating to positional displacement between the first composited image data and the second composited image data, using the first composited image data and the second composited image data; and
acquiring information relating to positional displacement of the first plurality of image data sets, using information relating to the positional displacement between the first composited image data and the second composited image data.

19. A non-transitory computer-readable storage medium storing a program to execute a method, the method comprising:
acquiring a first plurality of image data sets;
acquiring first composited image data using a first two or more image data sets of the first plurality of image data sets;
acquiring second composited image data, using a second two or more image data sets of the first plurality of image data sets, the second two or more image data sets being a combination different from the first two or more image data sets;
acquiring information relating to positional displacement between the first composited image data and the second composited image data, using the first composited image data and the second composited image data; and
acquiring information relating to positional displacement of the first plurality of image data sets, using information relating to the positional displacement between the first composited image data and the second composited image data.

* * * * *